(12) United States Patent
Briese et al.

(10) Patent No.: US 7,582,740 B2
(45) Date of Patent: Sep. 1, 2009

(54) METHODS AND KITS FOR DETECTING SARS-ASSOCIATED CORONAVIRUS

(75) Inventors: Thomas Briese, White Plains, NY (US); W. Ian Lipkin, New York, NY (US); Gustavo Palacios, New York, NY (US); Omar Jabado, New York, NY (US)

(73) Assignee: The Trustees of Columbia University In the City of New York, New York, NY (US)

( * ) Notice: Subject to any disclaimer, the term of this patent is extended or adjusted under 35 U.S.C. 154(b) by 0 days.

(21) Appl. No.: 10/764,075

(22) Filed: Jan. 23, 2004

(65) Prior Publication Data

US 2004/0265796 A1 Dec. 30, 2004

Related U.S. Application Data

(60) Provisional application No. 60/463,704, filed on Apr. 17, 2003.

(51) Int. Cl.
C07H 21/02 (2006.01)
C07H 21/04 (2006.01)
C12Q 1/70 (2006.01)
C12Q 1/68 (2006.01)

(52) U.S. Cl. .............................. 536/23.1; 435/5; 435/6; 536/23.7; 536/23.72; 536/24.3; 536/24.32; 536/24.33

(58) Field of Classification Search .............. 536/23.72, 536/24.32, 24.33; 435/5, 6
See application file for complete search history.

(56) References Cited

U.S. PATENT DOCUMENTS

2001/0053519 A1* 12/2001 Fodor et al. .................... 435/6

FOREIGN PATENT DOCUMENTS

WO WO 2004/092360 * 10/2004

OTHER PUBLICATIONS

Genbank Accession No. AY274119, "SARS Coronavirus Tor2, complete genome," version AY274119.1, Apr. 14, 2003.*
SARS-associated Coronavirus. Genomic Sequence Availablity. [online] [retreived on Jul. 11, 2005]. Retrieved from the Internet <URL:http://www.bcgsc.ca/bioinfo/SARS>.*
Ksiazek et al (New England Journal of Medicine 348(20):1953-1966, published online Apr. 10, 2003).*
Vabret et al (Journal of Virological Methods 97:59-66, 2001).*
Stewart et al (In: Y. Becker and G.Darai, Eds, Diagnosis of Human Viruses by Polymerase Chain Reaction Technology, Springer-Verlag, New York (1995), pp. 316-327).*
Pages 141-145 of appplication 60463109 (claimed for priority in above WO 2004/092360); filed Apr. 14, 2003.*
Calza L., Manfredi R., Verucchi G., Chiodo F. "SARS: a new emergency in the world health" Recenti Prog Med. 94(7-8): 284-294, 2003 (Abstract only).

Drosten et al., "Identification of a Novel Coronavirus in Patients with Severe Acute Respiratory Syndrome" N. Engl. J. Med., 348: 1967-1976, 2003.
Kaiser et al., "Viral aetiology of acute respiratory illness in patients with suspected severe acute respiratory syndrome (SARS) in Switzerland" Swiss Med. Wkly. 133: 400-401, 2003.
Ksiazek et al., "A Novel Coronavirus Associated With Severe Acute Respiratory Syndrome" N. Engl. J. Med., 348: 1953-1966, 2003.
Kuiken et al., "Newly discovered coronavirus as the primary cause of severe acute respiratory syndrome" Lancet 362: 263-270, 2003.
Lee et al., "A major outbreak of severe acute respiratory syndrome in Hong Kong" N. Engl. J. Med., 348: 1995-2005, 2003.
Li G., Chen X. and Xu A. "Profile of specific antibodies to the SARS-associated coronavirus" N. Eng. J. Med. 349: 5-6, 2003.
Mazzulli et al., "Severe acute respiratory syndrome-associated coronavirus in lung tissue" Emerg. Infect. Dis. 10: 20-24, 2004.
Peiris et al., "Coronavirus as a possible cause of severe acute respiratory syndrome in Hong Kong" Lancet, 361: 1319-1325, 2003.
Poutanen et al., "Identification of severe acute respiratory syndrome in Canada" N. Engl. J. Med., 348: 1995-2005, 2003.
Ren et al., "Detection of SARS-CoV RNA in stool samples of SARS patients by nest RT-PCR and its clinical value" Zhongguo YiXue Ke Xue Yuan Xue Bao 25: 368-371, 2003 (Abstract only).
"SARS" Weekly Epidemiological Record 78: 81-83, 2003.
WHO Multicentre Collaborative Network for Severe Acute Respiratory Syndrome (SARS) Diagnosis. A multicentre collaboration to investigate the cause of severe acute respiratory syndrome. Lancet 361: 1730-1733, 2003.
Wu et al., "Establishment of a fluorescent polymerase chain reaction method for the detection of the SARS-associated coronavirus and its clinical application". Chin. Med. J. 116: 988-990, 2003.

(Continued)

*Primary Examiner*—Bruce Campell
*Assistant Examiner*—Louise Humphrey
(74) *Attorney, Agent, or Firm*—Wilmer Cutler Pickering Hale and Dorr LLP

(57) ABSTRACT

The present invention provides a synthetic nucleic acid sequence comprising 10-30 nucleotides of the N gene region and/or the 3' non-coding region of the SARS-associated coronavirus genome, and a synthetic nucleic acid sequence comprising 10-30 nucleotides of a nucleic acid sequence that is complementary to at least one of those regions. Also provided are compositions comprising the sequences, and uses of the sequences in diagnostic kits. The present invention further provides a primer set for determining the presence or absence of SARS-associated coronavirus in a biological sample, wherein the primer set comprises at least one of the synthetic nucleic acid sequences. Also provided are a composition comprising the primer set, and use of the primer set in a diagnostic kit. Finally, the present invention provides kits and methods for determining the presence or absence of SARS-associated coronavirus in a biological sample.

71 Claims, 9 Drawing Sheets

OTHER PUBLICATIONS

Chin —"On the Preparation and Utilization of Isolated and Purified Oligonucleotides" (Mar. 9, 2002) (On deposit in the Katherine R. Everett Law Library at UNC).

Poon et al., "Early diagnosis of SARS coronavirus infection by real time Kf-PCR," J. Clin Virol, 28:233-238 (2003).

WHO Update 31, "Coronavirus never before seen in humans is the cause of SARS," Apr. 16, 2003.

Yam et al., "Evaluation of reverse transcription_PCR assays for rapid diagnosis of severe acute respiratory syndrome associated with a novel coronavirus," J. Clin. Microbiol. 41:4521-4524 (Oct. 2003).

Zhou et al., "Identification and molecular cloning and sequence analysis of novel coronavirus from patients with SARS by RT-PCR," Zhonghua Shi Yan Lin Chuang Bing Du Xue Za Zhi 17: 137-139 (Jun. 2003).

* cited by examiner

```
    TTATTAGGTTTTTACCTACCCAGGAAAAGCCAACCAACCTCGATCTCTTGTAGATCTGTT
1 ---------+---------+---------+---------+---------+---------+ 60
    AATAATCCAAAAATGGATGGGTCCTTTTCGGTTGGTTGGAGCTAGAGAACATCTAGACAA

CTCTAAACGAACTTTAAAATCTGTGTAGCTGTCGCTCGGCTGCATGCCTAGTGCACCTAC
61 ---------+---------+---------+---------+---------+---------+ 120
    GAGATTTGCTTGAAATTTTAGACACATCGACAGCGAGCCGACGTACGGATCACGTGGATG
```

...

```
       GTACTATGACAAATAGACAGTTTCATCAGAAATTATTGAAGTCAATAGCCGCCACTAGAG
15061 ---------+---------+---------+---------+---------+---------+ 15120
       CATGATACTGTTTATCTGTCAAAGTAGTCTTTAATAACTTCAGTTATCGGCGGTGATCTC

GAGCTACTGTGGTAATTGGAACAAGCAAGTTTTACGGTGGCTGGCATAATATGTTAAAAA
15121 ---------+---------+---------+---------+---------+---------+ 15180
       CTCGATGACACCATTAACCTTGTTCGTTCAAAATGCCACCGACCGTATTATACAATTTTT
                       CANADA first PCR  CA
       CTGTTTACAGTGATGTAGAAACTCCACACCTTATGGGTTGGGATTATCCAAAATGTGACA
15181 ---------+---------+---------+---------+---------+---------+ 15240
       GACAAATGTCACTACATCTTTGAGGTGTGGAATACCCAACCCTAATAGGTTTTACACTGT GAGCCATGCCTAACATG
       GAGCCATGCCTAACATGCTTAGGATAATGGCCTCTCTTGTTCTTGCTCGCAAACATAACA
15241 ---------+---------+---------+---------+---------+---------+ 15300
       CTCGGTACGGATTGTACGAATCCTATTACCGGAGAGAACAAGAACGAGCGTTTGTATTGT CTTGCTGTAACTTATCACACCGTTTCTACAGGTTAGCTAACGAGTGTGCGCAAGTATTAA
15301 ---------+---------+---------+---------+---------+---------+ 15360
       GAACGACATTGAATAGTGTGGCAAAGATGTCCAATCGATTGCTCACACGCGTTCATAATT
              CANADA second PCR  TGTTAAACCAGGTGGAAC
       GTGAGATGGTCATGTGTGGCGGCTCACTATATGTTAAACCAGGTGGAACATCATCCGGTG
15361 ---------+---------+---------+---------+---------+---------+ 15420
       CACTCTACCAGTACACACCGCCGAGTGATATACAATTTGGTCCACCTTGTAGTAGGCCAC ATGCTACAACTGCTTATGCTAATAGTGTCTTTAACATTTGTCAAGCTGTTACAGCCAATG
15421 ---------+---------+---------+---------+---------+---------+ 15480
       TACGATGTTGACGAATACGATTATCACAGAAATTGTAAACAGTTCGACAATGTCGGTTAC TAAATGCACTTCTTTCAACTGATGGTAATAAGATAGCTGACAAGTATGTCCGCAATCTAC
15481 ---------+---------+---------+---------+---------+---------+ 15540
       ATTTACGTGAAGAAAGTTGACTACCATTATTCTATCGACTGTTCATACAGGCGTTAGATG
                         GCGTTAGATG
```

FIG. 1

```
             AACACAGGCTCTATGAGTGTCTCTATAGAAATAGGGATGTTGATCATGAATTCGTGGATG
15541 ---------+---------+---------+---------+---------+---------+ 15600
             TTGTGTCCGAGATACTCACAGAGATATCTTTATCCCTACAACTAGTACTTAAGCACCTAC
             TTGTGTCC CANADA second PCR AGTTTTACGCTTACCTGCGTAAACATTTCTCCATGATGATTCTTTCTGATGATGCCGTTG
15601 ---------+---------+---------+---------+---------+---------+ 15660
             TCAAAATGCGAATGGACGCATTTGTAAAGAGGTACTACTAAGAAAGACTACTACGGCAAC
                 GCGAATGGACGCATTTGTAA CANADA first PCR TGTGCTATAACAGTAACTATGCGGCTCAAGGTTTAGTAGCTAGCATTAAGAACTTTAAGG
15661 ---------+---------+---------+---------+---------+---------+ 15720
             ACACGATATTGTCATTGATACGCCGAGTTCCAAATCATCGATCGTAATTCTTGAAATTCC CAGTTCTTTATTATCAAAATAATGTGTTCATGTCTGAGGCAAAATGTTGGACTGAGACTG
15721 ---------+---------+---------+---------+---------+---------+ 15780
             GTCAAGAAATAATAGTTTTATTACACAAGTACAGACTCCGTTTTACAACCTGACTCTGAC
```

...

```
             GTAGTAAGATCATTACTGGTCTTCATCCTACACAGGCACCTACACACCTCAGCGTTGATA
18001 ---------+---------+---------+---------+---------+---------+ 18060
             CATCATTCTAGTAATGACCAGAAGTAGGATGTGTCCGTGGATGTGTGGAGTCGCAACTAT

TAAAGTTCAAGACTGAAGGATTATGTGTTGACATACCAGGCATACCAAAGGACATGACCT
18061 ---------+---------+---------+---------+---------+---------+ 18120
             ATTTCAAGTTCTGACTTCCTAATACACAACTGTATGGTCCGTATGGTTTCCTGTACTGGA

BNIoutS2 ATGAATTACCAAGTCAATGGTTAC
             ACCGTAGACTCATCTCTATGATGGGTTTCAAAATGAATTACCAAGTCAATGGTTACCCTA
18121 ---------+---------+---------+---------+---------+---------+ 18180
             TGGCATCTGAGTAGAGATACTACCCAAAGTTTTACTTAATGGTTCAGTTACCAATGGGAT BNIinS GAAGCTATTCGTCACGTTCG
             ATATGTTTATCACCCGCGAAGAAGCTATTCGTCACGTTCGTGCGTGGATTGGCTTTGATG
18181 ---------+---------+---------+---------+---------+---------+ 18240
             TATACAAATAGTGGGCGCTTCTTCGATAAGCAGTGCAAGCACGCACCTAACCGAAACTAC TAGAGGGCTGTCATGCAACTAGAGATGCTGTGGGTACTAACCTACCTCTCCAGCTAGGAT
18241 ---------+---------+---------+---------+---------+---------+ 18300
             ATCTCCCGACAGTACGTTGATCTCTACGACACCCATGATTGGATGGAGAGGTCGATCCTA
                                                          GAGGTCGATCCTA TTTCTACAGGTGTTAACTTAGTAGCTGTACCGACTGGTTATGTTGACACTGAAAATAACA
18301 ---------+---------+---------+---------+---------+---------+ 18360
             AAAGATGTCCACAATTGAATCATCGACATGGCTGACCAATACAACTGTGACTTTTATTGT
             AAAGATGTC BNIinAS
                         CATCGACATGGCTGACCAATAC BNIoutAS
```

FIG. 1 cont.

```
         CAGAATTCACCAGAGTTAATGCAAAACCTCCACCAGGTGACCAGTTTAAACATCTTATAC
18361 ---------+---------+---------+---------+---------+---------+ 18420
         GTCTTAAGTGGTCTCAATTACGTTTTGGAGGTGGTCCACTGGTCAAATTTGTAGAATATG

CACTCATGTATAAAGGCTTGCCCTGGAATGTAGTGCGTATTAAGATAGTACAAATGCTCA
18421 ---------+---------+---------+---------+---------+---------+ 18480
         GTGAGTACATATTTCCGAACGGGACCTTACATCACGCATAATTCTATCATGTTTACGAGT

...

TACCGAAGAGCTACCCGACGAGTTCGTGGTGGTGACGGCAAAATGAAAGAGCTCAGCCCC
28381 ---------+---------+---------+---------+---------+---------+ 28440
         ATGGCTTCTCGATGGGCTGCTCAAGCACCACCACTGCCGTTTTACTTTCTCGAGTCGGGG

AGATGGTACTTCTATTACCTAGGAACTGGCCCAGAAGCTTCACTTCCCTACGGCGCTAAC
28441 ---------+---------+---------+---------+---------+---------+ 28500
         TCTACCATGAAGATAATGGATCCTTGACCGGGTCTTCGAAGTGAAGGGATGCCGCGATTG

CIID-28506F AGGCATCGTATGGGTTGCA
            CIID-28529T AGGGAGCCTTGAATACACCCAAAGACCA
         AAAGAAGGCATCGTATGGGTTGCAACTGAGGGAGCCTTGAATACACCCAAAGACCACATT
28501 ---------+---------+---------+---------+---------+---------+ 28560
         TTTCTTCCGTAGCATACCCAACGTTGACTCCCTCGGAACTTATGTGGGTTTCTGGTGTAA

GGCACCCGCAATCCTAATAACAATGCTGCCACCGTGCTACAACTTCCTCAAGGAACAACA
28561 ---------+---------+---------+---------+---------+---------+ 28620
         CCGTGGGCGTTAGGATTATTGTTACGACGGTGGCACGATGTTGAAGGAGTTCCTTGTTGT
                                                                  TTGTTGT

TTGCCAAAAGGCTTCTACGCAGAGGGAAGCAGAGGCGGCAGTCAAGCCTCTTCTCGCTCC
28621 ---------+---------+---------+---------+---------+---------+ 28680
         AACGGTTTTCCGAAGATGCGTCTCCCTTCGTCTCCGCCGTCAGTCGGAGAAGAGCGAGG
         AACGGTTTTCCGAAG CIID-28614R

TCATCACGTAGTCGCGGTAATTCAAGAAATTCAACTCCTGGCAGCAGTAGGGGAAATTCT
28681 ---------+---------+---------+---------+---------+---------+ 28740
         AGTAGTGCATCAGCGCCATTAAGTTCTTTAAGTTGAGGACCGTCGTCATCCCCTTTAAGA

CCTGCTCGAATGGCTAGCGGAGGTGGTGAAACTGCCCTCGCGCTATTGCTGCTAGACAGA
28741 ---------+---------+---------+---------+---------+---------+ 28800
         GGACGAGCTTACCGATCGCCTCCACCACTTTGACGGGAGCGCGATAACGACGATCTGTCT

TTGAACCAGCTTGAGAGCAAAGTTTCTGGTAAAGGCCAACAACAACAAGGCCAAACTGTC
28801 ---------+---------+---------+---------+---------+---------+ 28860
         AACTTGGTCGAACTCTCGTTTCAAAGACCATTTCCGGTTGTTGTTGTTCCGGTTTGACAG

CIID-28891F AAGCCTCGCCAAAAACGTAC
         ACTAAGAAATCTGCTGCTGAGGCATCTAAAAAGCCTCGCCAAAAACGTACTGCCACAAAA
28861 ---------+---------+---------+---------+---------+---------+ 28920
         TGATTCTTTAGACGACGACTCCGTAGATTTTTCGGAGCGGTTTTTGCATGACGGTGTTTT
```

FIG. 1 cont.

```
            CAGTACAACGTCACTCAAGCATTTGGGAGACGTGGTCCAGAACAAACCCAAGGAAATTTC
28921 ---------+---------+---------+---------+---------+---------+ 28980
            GTCATGTTGCAGTGAGTTCGTAAACCCTCTGCACCAGGTCTTGTTTGGGTTCCTTTAAAG

GGGGACCAAGACCTAATCAGACAAGGAACTGATTACAAACATTGGCCGCAAATTGCACAA
28981 ---------+---------+---------+---------+---------+---------+ 29040
            CCCCTGGTTCTGGATTAGTCTGTTCCTTGACTAATGTTTGTAACCGGCGTTTAACGTGTT

CIID-29074T TCACGCATTGGCATGGAAGTCACAC
            TTTGCTCCAAGTGCCTCTGCATTCTTTGGAATGTCACGCATTGGCATGGAAGTCACACCT
29041 ---------+---------+---------+---------+---------+---------+ 29100
            AAACGAGGTTCACGGAGACGTAAGAAACCTTACAGTGCGTAACCGTACCTTCAGTGTGGA
                                                 A

TCGGGAACATGGCTGACTTATCATGGAGCCATTAAATTGGATGACAAAGATCCACAATTC
29101 ---------+---------+---------+---------+---------+---------+ 29160
            AGCCCTTGTACCGACTGAATAGTACCTCGGTAATTTAACCTACTGTTTCTAGGTGTTAAG
            AGCCCTTGTACCGACTGAA CIID-29100R

AAAGACAACGTCATACTGCTGAACAAGCACATTGACGCATACAAAACATTCCCACCAACA
29161 ---------+---------+---------+---------+---------+---------+ 29220
            TTTCTGTTGCAGTATGACGACTTGTTCGTGTAACTGCGTATGTTTTGTAAGGGTGGTTGT

GAGCCTAAAAAGGACAAAAAGAAAAAGACTGATGAAGCTCAGCCTTTGCCGCAGAGACAA
29221 ---------+---------+---------+---------+---------+---------+ 29280
            CTCGGATTTTTCCTGTTTTTCTTTTTCTGACTACTTCGAGTCGGAAACGGCGTCTCTGTT

AAGAAGCAGCCCACTGTGACTCTTCTTCCTGCGGCTGACATGGATGATTTCTCCAGACAA
29281 ---------+---------+---------+---------+---------+---------+ 29340
            TTCTTCGTCGGGTGACACTGAGAAGAAGGACGCCGACTGTACCTACTAAAGAGGTCTGTT

CIID-29398F ATG
            CTTCAAAATTCCATGAGTGGAGCTTCTGCTGATTCAACTCAGGCATAAACACTCATGATG
29341 ---------+---------+---------+---------+---------+---------+ 29400
            GAAGTTTTAAGGTACTCACCTCGAAGACGACTAAGTTGAGTCCGTATTTGTGAGTACTAC

CIID-29426F AAACGTTTTCGCAATTCCGT
       CIID-29405F CACAAGGCAGATGGGCTATGT
            ACCACACAAGGCACATGG
            ACCACACAAGGCAGATGGGCTATGTAAACGTTTTCGCAATTCCGTTTACGATACATAGTC
29401 ---------+---------+---------+---------+---------+---------+ 29460
            TGGTGTGTTCCGTCTACCCGATACATTTGCAAAAGCGTTAAGGCAAATGCTATGTATCAG

TACTCTTGTGCAGAATGAATTCTCGTAACTAAACAGCACAAGTAGGTTTAGTTAACTTTA
29461 ---------+---------+---------+---------+---------+---------+ 29520
            ATGAGAACACGTCTTACTTAAGAGCATTGATTTGTCGTGTTCATCCAAATCAATTGAAAT

ATCTCACATAGCAATCTTTAATCAATGTGTAACATTAGGGAGGACTTGAAAGAGCCACCA
29521 ---------+---------+---------+---------+---------+---------+ 29580
            TAGAGTGTATCGTTAGAAATTAGTTACACATTGTAATCCCTCCTGAACTTTCTCGGTGGT
```

FIG. 1 cont.

```
CIID-29584T TTTCATCGAGGCCACGCGGAGTAC
     CATTTTCATCGAGGCCACGCGGAGTACGATCGAGGGTACAGTGAATAATGCTAGGGAGAG
29581 ---------+---------+---------+---------+---------+---------+ 29640
     GTAAAAGTAGCTCCGGTGCGCCTCATGCTAGCTCCCATGTCACTTATTACGATCCCTCTC
                              TGTCACTTATTGCGATCCCTCTC
                               GTCACTTATTGCGATCCCTCTC
                              TGTCACTTATTACGATCCCTCTC
                                 CTTATTACGATCCCTCTC
            TCCGGTGCGCCTCATGCTAGCT CIID-29592T

CTGCCTATATGGAAGAGCCCTAATGTGTAAAATTAATTTTAGTAGTGCTATCCCCATGTG
29641 ---------+---------+---------+---------+---------+---------+ 29700
     GACGGATATACCTTCTCGGGATTACACATTTTAATTAAAATCATCACGATAGGGGTACAC
     G 29618R
     G 29619R
     G 29618-2R
     GACGG CIID-29623R

ATTTTAATAGCTTCTTAGGAGAATGAC
29701 ---------+---------+------- 29727
     TAAAATTATCGAAGAATCCTCTTACTG
```

FIG. 1 cont.

```
AGGCATCGTATGGGTTGCAACTGAGGGAGCCTTGAATACACCCAAAGACCACATTGGCACCCGCA
ATCCTAATAACAATGCTGCCACCGTGCTACAACTTCCTCAAGGAACAACATTGCCAAAAGGCTTCT
ACGCAGAGGGAAGCAGAGGCGGCAGTCAAGCCTCTTCTCGCTCCTCATCACGTAGTCGCGGTAAT
TCAAGAAATTCAACTCCTGGCAGCAGTAGGGGAAATTCTCCTGCTCGAATGGCTAGCGGAGGTGG
TGAAACTGCCCTCGCGCTATTGCTGCTAGACAGATTGAACCAGCTTGAGAGCAAAGTTTCTGGTAA
AGGCCAACAACAACAAGGCCAAACTGTCACTAAGAAATCTGCTGCTGAGGCATCTAAAAAGCCTC
GCCAAAAACGTACTGCCACAAAACAGTACAACGTCACTCAAGCATTTGGGAGACGTGGTCCAGAA
CAAACCCAAGGAAATTTCGGGGACCAAGACCTAATCAGACAAGGAACTGATTACAAACATTGGCC
GCAAATTGCACAATTTGCTCCAAGTGCCTCTGCATTCTTTGGAATGTCACGCATTGGCATGGAAGT
CACACCTTCGGGAACATGGCTGACTTATCATGGAGCCATTAAATTGGATGACAAAGATCCACAATT
CAAAGACAACGTCATACTGCTGAACAAGCACATTGACGCATACAAAACATTCCCACCAACAGAGC
CTAAAAAGGACAAAAAGAAAAAGACTGATGAAGCTCAGCCTTTGCCGCAGAGACAAAAGAAGCA
GCCCACTGTGACTCTTCTTCCTGCGGCTGACATGGATGATTTCTCCAGACAACTTCAAAATTCCATG
AGTGGAGCTTCTGCTGATTCAACTCAGGCATAAACACTCATGATGACCACACAAGGCAGATGGGC
TATGTAAACGTTTTCGCAATTCCGTTTACGATACATAGTCTACTCTTGTGCAGAATGAATTCTCGTA
ACTAAACAGCACAAGTAGGTTTAGTTAACTTTAATCTCACATAGCAATCTTTAATCAATGTGTAAC
ATTAGGGAGGACTTGAAAGAGCCACCACATTTTCATCGAGGCCACGCGGAGTACGATCGAGGGTA
CAGTGAATAATGCTAGGGAGAGC
```

FIG. 3

FIG. 4
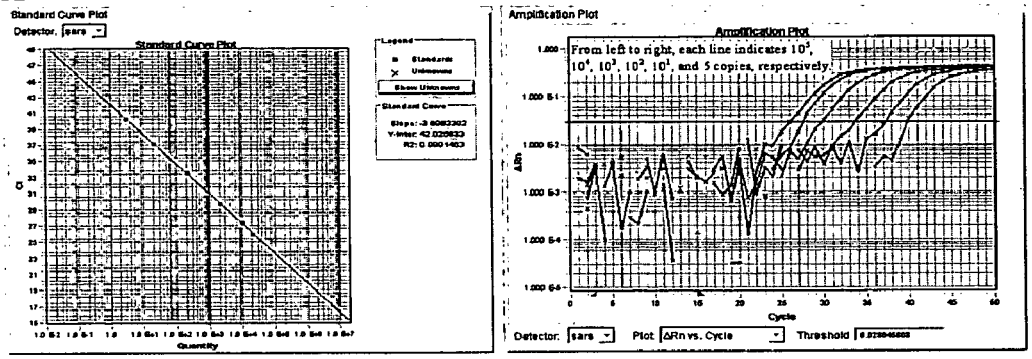
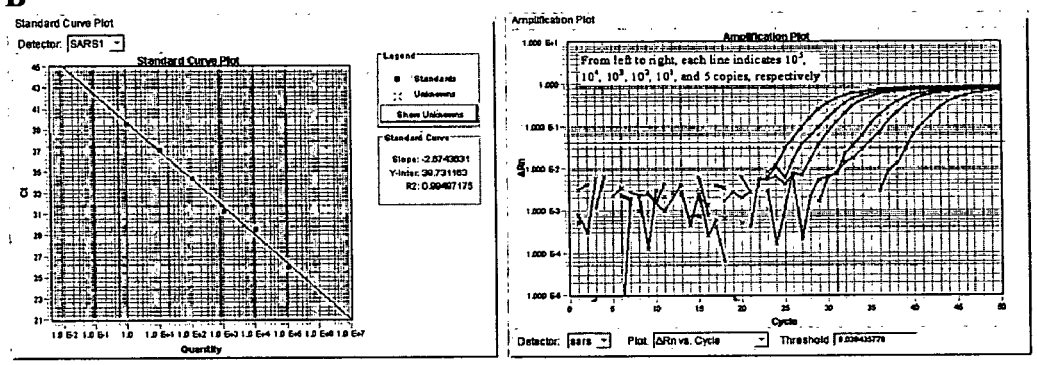

METHODS AND KITS FOR DETECTING SARS-ASSOCIATED CORONAVIRUS

RELATED APPLICATIONS

This application claims the benefit of U.S. Provisional Application Ser. No. 60/463,704, filed on Apr. 17, 2003, and entitled "METHODS AND KITS FOR DETECTING SARS-ASSOCIATED CORONAVIRUS", the contents of which are hereby incorporated by reference herein.

STATEMENT OF GOVERNMENT INTEREST

This invention was made with government support under NIH Grant Nos. AI51292 and U54 AI057158. As such, the United States government may have certain rights in this invention.

BACKGROUND OF THE INVENTION

Severe acute respiratory syndrome (SARS) is a new, potentially life threatening infectious disease of humans. After SARS was first recognized in late February 2003 in Hanoi, Vietnam, the disease spread rapidly, with cases reported from 29 countries on five continents over 4 months (World Health Organization. Severe acute respiratory syndrome (SARS I. *Wkly. Epidemiol. Rec.* 2003, 78:81-3; Peiris, et al. Coronavirus as a possible cause of severe acute respiratory syndrome. *Lancet* 2003, 361:1319-25; Lee, et al. A major outbreak of severe acute respiratory syndrome in Hong Kong. *N. Eng. J. Med.* 2003, 348:1986-94; Tsang, et al. A cluster of cases of severe acute respiratory syndrome in Hong Kong. *N. Eng. J. Med.* 2003, 348:1977-85; Poutanen, et al. Identification of severe acute respiratory syndrome in Canada. *N. Eng. J. Med.* 2003, 348:1995-2005; Kuiken, et al. Newly discovered coronavirus as the primary cause of severe acute respiratory syndrome. *Lancet* 2003, 362:263-70; World Health Organization Multicentre Collaborative Network for Severe Acute Respiratory Syndrome (SARS) Diagnosis. A multicentre collaboration to investigate the cause of severe acute respiratory syndrome. *Lancet* 2003, 361:1730-3). By Jul. 3, 2003, this epidemic resulted in 8,439 reported cases globally, of which 812 were fatal (Cumulative number of reported probable cases of severe acute respiratory syndrome (SARS). e-publication cited Jul. 8, 2003).

The most common early symptoms of SARS include fever (a measured temperature greater than 100.4° F. (38.0° C.)), chills, headache, myalgia, dizziness, rigors, cough, sore throat, and runny nose (*WHO Weekly Epidemiological Record*, No. 12, Mar. 21, 2003). The SARS illness usually starts with fever, severe headache, dizziness, and myalgia. After 2 to 7 days, SARS patients generally develop a dry, nonproductive cough. In some cases, there may be rapid deterioration of conditions, with low oxygen saturation and acute respiratory distress.

The SARS-associated coronavirus pathogen was quickly isolated, and its genome has been sequenced by scientists in Canada and the United States (Ksiazek et al., A novel coronavirus associated with severe acute respiratory syndrome. *N. Engl. J. Med.*, Apr. 10, 2003, e-pub; Drosten et al., Identification of a novel coronavirus in patients with severe acute respiratory syndrome. *N. Engl. J. Med.*, Apr. 10, 2003, e-pub; *WHO Update* 31, Coronavirus never before seen in humans is the cause of SARS, Apr. 16, 2003). Rapid identification of the causal agent as a novel coronavirus (SARS-CoV) represents an extraordinary achievement in the history of global health and helped to contain the epidemic (World Health Organization Multicentre Collaborative Network for Severe Acute Respiratory Syndrome (SARS) Diagnosis. A multicentre collaboration to investigate the cause of severe acute respiratory syndrome. *Lancet* 2003 361:1730-3). Nonetheless, the epidemiology and pathogenesis of SARS remain poorly understood, and definitive diagnostic tests or specific treatments are not established. Since the origin of the virus and its animal reservoirs remain to be defined, the potential for recurrence is unknown. This fact underscores the importance of establishing sensitive and efficient methods for diagnosis and surveillance.

The coronavirus that has been implicated in SARS represents the prototype of a new lineage of coronaviruses capable of causing outbreaks of clinically significant and frequently fatal human disease. Coronaviruses were first isolated from chicken in 1937, and from human in 1965. The coronavirus family contains approximately 15 species, which infect a broad range of animals, including humans, cats, dogs, cows, pigs, rodents, and birds (e.g., chickens). The coronavirus is a single-stranded, (+)sense RNA virus. The virus enters the host cell via endocytosis, and reproduces itself in the cytoplasm; no DNA stage is involved. New virions form by budding into the Golgi apparatus, being transported to the cell surface, and secreted from host cell.

To date, there is only a limited repertoire of sensitive, specific diagnostic assays available that allow surveillance and clinical management of SARS and SARS-associated diseases. As specific antiviral therapies are established, early diagnosis will be increasingly important in minimizing morbidity and mortality. Immunofluorescence and enzyme-linked immunosorbent assays (ELISA) are reported to inconsistently detect antibodies to SARS-CoV before day 10 or 20 after the onset of symptoms, respectively (World Health Organization Multicentre Collaborative Network for Severe Acute Respiratory Syndrome (SARS) Diagnosis. A multicentre collaboration to investigate the cause of severe acute respiratory syndrome. *Lancet* 2003, 361:1730-3; Li G Chen X and Xu A. Profile of specific antibodies to the SARS-associated coronavirus. *N. Eng. J. Med.* 2003, 349:5-6). Thus, although helpful in tracking the course of infection at the population level, these serologic tools have less usefulness in detecting infection at early stages, when there may be potential to implement therapeutic interventions or measures, such as quarantine that may reduce the risk for transmission to naive persons. In contrast, polymerase chain reaction (PCR)-based assays have the potential to detect SARS and SARS-associated infection at earlier time points. However, a need exists for a sensitive, reliable, and rapid diagnostic method for detecting the presence of the SARS-associated coronavirus in a biological sample at the earliest possible stage of infection.

SUMMARY OF THE INVENTION

The inventors have developed a PCR and real-time PCR assay that can be readily standardized across laboratories for detection of the SARS-associated coronavirus. In particular, the inventors' assay allows rapid molecular detection of the SARS-associated coronavirus, and has improved sensitivity and specificity with respect to other molecular assays or serological assays, including those assays directed to the SARS-associated coronavirus polymerase gene. This sensitive molecular tool may be used to diagnose infection with the SARS-associated coronavirus.

Accordingly, the present invention provides a synthetic nucleic acid sequence comprising 10-30 consecutive nucleotides of at least one of the following: (a) the N gene region of the SARS-associated coronavirus genome; and (b) the 3' noncoding region of the SARS-associated coronavirus genome. Also provided are a composition comprising the synthetic nucleic acid sequence, and use of the synthetic nucleic acid sequence in a kit for determining the presence or absence of SARS-associated coronavirus in a biological sample.

The present invention further provides a synthetic nucleic acid sequence comprising 10-30 consecutive nucleotides of a nucleic acid sequence that is complementary to at least one of the following: (a) the N gene region of the SARS-associated coronavirus genome; and (b) the 3' non-coding region of the SARS-associated coronavirus genome. Also provided are a composition comprising the synthetic nucleic acid sequence, and use of the synthetic nucleic acid sequence in a kit for determining the presence or absence of SARS-associated coronavirus in a biological sample.

The present invention also provides a synthetic nucleic acid sequence comprising 10-30 consecutive nucleotides of the nucleic acid sequence of SEQ ID NO:1 or of a nucleic acid sequence that is complementary to the nucleic acid sequence of SEQ ID NO:1.

Additionally, the present invention provides a primer set for determining the presence or absence of SARS-associated coronavirus in a biological sample, wherein the primer set comprises at least one synthetic nucleic acid sequence selected from the group consisting of: (a) a synthetic nucleic acid sequence comprising 10-30 consecutive nucleotides of at least one of the following: (i) the N gene region of the SARS-associated coronavirus genome; and (ii) the 3' non-coding region of the SARS-associated coronavirus genome; and (b) a synthetic nucleic acid sequence comprising 10-30 consecutive nucleotides of a nucleic acid sequence that is complementary to at least one of the following: (i) the N gene region of the SARS-associated coronavirus genome; and (ii) the 3' non-coding region of the SARS-associated coronavirus genome. In one embodiment of the invention, the at least one synthetic nucleic acid sequence has a nucleotide sequence selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, and SEQ ID NO:16, and a fragment, variant, and derivative thereof. Also provided are a composition comprising the primer set, and use of the primer set in a kit for determining the presence or absence of SARS-associated coronavirus in a biological sample.

The present invention also provides a kit for determining the presence or absence of SARS-associated coronavirus in a biological sample, comprising at least one synthetic nucleic acid sequence and instructions for use, wherein the at least one synthetic nucleic acid sequence is selected from the group consisting of: (a) a nucleic acid sequence comprising 10-30 consecutive nucleotides of at least one of the following: (i) the N gene region of the SARS-associated coronavirus genome; and (ii) the 3' non-coding region of the SARS-associated coronavirus genome; and (b) a nucleic acid sequence comprising 10-30 consecutive nucleotides of a nucleic acid sequence that is complementary to at least one of the following: (i) the N gene region of the SARS-associated coronavirus genome; and (ii) the 3' non-coding region of the SARS-associated coronavirus genome.

The present invention further provides a kit for determining the presence or absence of SARS-associated coronavirus in a biological sample, comprising: (a) a primer set comprising at least two nucleic acid sequences, wherein at least one of the at least two nucleic acid sequences is selected from the group consisting of: (i) a nucleic acid sequence comprising 10-30 consecutive nucleotides of at least one of the following: (A) the N gene region of the SARS-associated coronavirus genome; and (B) the 3' non-coding region of the SARS-associated coronavirus genome; and (ii) a nucleic acid sequence comprising 10-30 consecutive nucleotides of a nucleic acid sequence that is complementary to at least one of the following: (A) the N gene region of the SARS-associated coronavirus genome; and (B) the 3' non-coding region of the SARS-associated coronavirus genome; and (b) instructions for use.

Finally, the present invention provides a method for determining the presence or absence of SARS-associated coronavirus in a biological sample, by: (a) contacting the biological sample with at least one synthetic nucleic acid sequence, under conditions suitable for amplification; and (b) determining the presence or absence of SARS-associated coronavirus in the biological sample; wherein the at least one synthetic nucleic acid sequence is selected from the group consisting of: (i) a nucleic acid sequence comprising 10-30 consecutive nucleotides at least one of the following: (A) the N gene region of the SARS-associated coronavirus genome; and (B) the 3' non-coding region of the SARS-associated coronavirus genome; and (ii) a nucleic acid sequence comprising 10-30 consecutive nucleotides of a nucleic acid sequence that is complementary to at least one of the following: (A) the N gene region of the SARS-associated coronavirus genome; and (B) the 3' non-coding region of the SARS-associated coronavirus genome.

Additional aspects of the present invention will be apparent in view of the description which follows.

BRIEF DESCRIPTION OF THE FIGURES

FIG. 1 depicts the SARS-associated coronavirus genome (SEQ ID NOS:40-43, respectively in order of appearance and various primers (SEQ ID NOS:27, 19, 28-29, 21, 23, 30-31, 11, 13, 32, 14, 16, 66, 8, 4, 34, 6 and 35-39, respectively in order of appearance).

FIG. 3 sets forth a nucleic acid sequence that includes the 3' non-coding region of the SARS-associated coronavirus genome and a portion of the N gene of the SARS-associated coronavirus genome (28506-29641 nt) (SEQ ID NO:1).

FIG. 4(A) depicts a standard curve and amplification plot using serial dilutions of plasmid DNA.

FIG. 4(B) shows a standard curve and amplification plot using serial dilutions of cRNA.

DETAILED DESCRIPTION OF THE INVENTION

Figure 2:
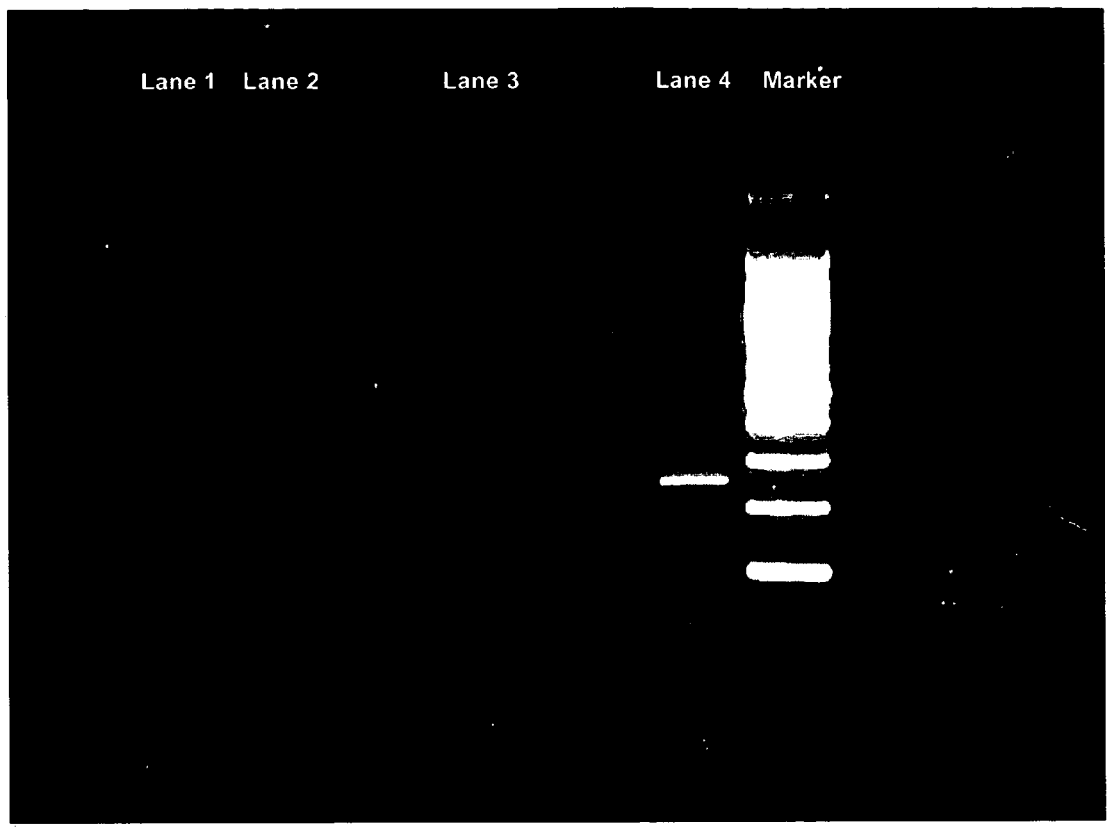
FIG. 2 sets forth the results of a comparison of the inventors' PCR method and primers (lane 3 and 4) with known PCR methods and primers (lane 1: Canada; lane 2: Germany).

The present invention is directed to novel synthetic nucleic acid sequences and PCR primers for use in detecting the presence or absence of SARS-associated coronavirus. The inventors' sequences and primers are more specific and more sensitive than those currently existing in the art. They also increase the speed of the PCR assay, as only one PCR step is required, and nesting is not involved.

Accordingly, the present invention provides a synthetic nucleic acid sequence comprising 10-30 consecutive nucleotides of at least one of the following: (a) the N gene region of the SARS-associated coronavirus genome; and (b) the 3' non-coding region of the SARS-associated coronavirus genome.

As used herein, a "nucleic acid" or "polynucleotide" includes a nucleic acid, an oligonucleotide, a nucleotide, a polynucleotide, and any fragment, variant, or derivative thereof. The nucleic acid or polynucleotide may be double-stranded, single-stranded, or triple-stranded DNA or RNA (including cDNA), or a DNA-RNA hybrid of genetic or synthetic origin, wherein the nucleic acid contains any combination of deoxyribonucleotides and ribonucleotides and any combination of bases, including, but not limited to, adenine, thymine, cytosine, guanine, uracil, inosine, and xanthine hypoxanthine. The nucleic acid or polynucleotide may be combined with a carbohydrate, a lipid, a protein, or other materials. A nucleic acid sequence of interest may be chemically synthesized using one of a variety of techniques known to those skilled in the art, including, without limitation, automated synthesis of oligonucleotides having sequences which correspond to a partial sequence of the nucleotide sequence of interest, or a variation sequence thereof, using commercially-available oligonucleotide synthesizers, such as the Applied Biosystems Model 392 DNA/RNA synthesizer.

The "complement" of a nucleic acid sequence refers, herein, to a nucleic acid molecule which is completely complementary to another nucleic acid, or which will hybridize to the other nucleic acid under conditions of high stringency. High-stringency conditions are known in the art (see, e.g., Maniatis et al., *Molecular Cloning: A Laboratory Manual,* 2nd ed. (Cold Spring Harbor: Cold Spring Harbor Laboratory, 1989) and Ausubel et al., eds., *Current Protocols in Molecular Biology* (New York, N.Y.: John Wiley & Sons, Inc., 2001)). Stringent conditions are sequence-dependent, and may vary depending upon the circumstances. As used herein, the term "cDNA" refers to an isolated DNA polynucleotide or nucleic acid molecule, or any fragment, derivative, or complement thereof. It may be double-stranded, single-stranded, or triple-stranded, it may have originated recombinantly or synthetically, and it may represent coding and/or noncoding 5' and/or 3' sequences.

The nucleic acid sequence set forth in FIG. 3 (SEQ ID NO:1) includes the 3' non-coding region of the SARS-associated coronavirus genome, and a portion of the neighboring N gene region of the genome. It is believed that the inventors' sequences will be useful in the detection and diagnosis of SARS-associated coronavirus. Therefore, the present invention also provides use of the synthetic nucleic acid sequence in a kit for determining the presence or absence of SARS-associated coronavirus in a biological sample. Examples of such a kit are described herein. Additionally, the present invention provides a composition comprising the above-described synthetic nucleic acid sequence (e.g., a composition comprising the synthetic nucleic acid sequence and a label or detectable marker).

The present invention further provides a synthetic nucleic acid sequence comprising 10-30 consecutive nucleotides of a nucleic acid sequence that is complementary to at least one of the following: (a) the N gene region of the SARS-associated coronavirus genome; and (b) the 3' non-coding region of the SARS-associated coronavirus genome. Also provided are a composition comprising the synthetic nucleic acid sequence, and use of the synthetic nucleic acid sequence in a kit for determining the presence or absence of SARS-associated coronavirus in a biological sample.

The present invention provides a synthetic nucleic acid sequence comprising 10-30 consecutive nucleotides of the nucleic acid sequence of SEQ ID NO:1. Also provided is a synthetic nucleic acid sequence comprising 10-30 consecutive nucleotides of a nucleic acid sequence that is complementary to the nucleic acid sequence of SEQ ID NO:1.

In addition, the present invention provides a primer set for determining the presence or absence of SARS-associated coronavirus in a biological sample. A primer is a short, pre-existing polynucleotide chain to which new deoxyribonucleotides may be added by DNA polymerase. The primer set of the present invention comprises at least one synthetic nucleic acid sequence selected from the group consisting of: (a) a synthetic nucleic acid sequence comprising 10-30 consecutive nucleotides of at least one of the following: (i) the N gene region of the SARS-associated coronavirus genome; and (ii) the 3' non-coding region of the SARS-associated coronavirus genome; and (b) a synthetic nucleic acid sequence comprising 10-30 consecutive nucleotides of a nucleic acid sequence that is complementary to at least one of the following: (i) the N gene region of the SARS-associated coronavirus genome; and (ii) the 3' non-coding region of the SARS-associated coronavirus genome. Also provided are a composition comprising the primer set, and use of the primer set in a kit for determining the presence or absence of SARS-associated coronavirus in a biological sample.

In one embodiment of the present invention, the at least one synthetic nucleic acid sequence of the present invention has a nucleotide sequence selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, and SEQ ID NO:16, and a fragment, variant, and derivative thereof. A derivative of the nucleic acid sequence of the present invention may be, for example, a nucleic acid sequence that has been modified for use in a fluorescent PCR assay.

In another embodiment of the present invention, the synthetic nucleic acid sequence of the primer set is derived from the 3' non-coding region of the SARS-associated coronavirus genome, or is the complement thereof. In one preferred embodiment, the at least one synthetic nucleic acid sequence of the present invention has the nucleotide sequence of SEQ ID NO:2, or a fragment, variant, or derivative thereof. In another preferred embodiment, the at least one synthetic nucleic acid sequence of the present invention has the nucleotide sequence of SEQ ID NO:3, or a fragment, variant, or derivative thereof. In yet another preferred embodiment, the at least one synthetic nucleic acid sequence of the present invention has the nucleotide sequence of SEQ ID NO:4, or a fragment, variant, or derivative thereof. In still another preferred embodiment, the at least one synthetic nucleic acid sequence of the present invention has the nucleotide sequence of SEQ ID NO:5, or a fragment, variant, or derivative thereof. In yet another preferred embodiment, the at least one synthetic nucleic acid sequence of the present invention has the nucleotide sequence of SEQ ID NO:6, or a fragment, variant, or derivative thereof. In still another preferred embodiment, the at least one synthetic nucleic acid sequence of the present invention has the nucleotide sequence of SEQ ID NO:7, or a fragment, variant, or derivative thereof. In a further preferred embodiment, the at least one synthetic nucleic acid sequence of the present invention has the nucleotide sequence of SEQ ID NO:8, or a fragment, variant, or derivative thereof. In yet another preferred embodiment, the at least one synthetic nucleic acid sequence has the nucleotide sequence of SEQ ID NO:9, or a fragment, variant, or derivative thereof. In still another preferred embodiment, the at least one synthetic nucleic acid sequence of the present invention has the nucleotide sequence of SEQ ID NO:10, or a fragment, variant, or derivative thereof.

In yet another embodiment of the present invention, the synthetic nucleic acid sequence of the primer set is derived from a portion of the N gene region of the SARS-associated coronavirus (or portions of the 3' non-coding region and the N gene region of the SARS-associated coronavirus), or is the complement thereof. In one preferred embodiment, the at least one synthetic nucleic acid sequence of the present invention has the nucleotide sequence of SEQ ID NO:11, or a fragment, variant, or derivative thereof. In another preferred embodiment, the at least one synthetic nucleic acid sequence of the present invention has the nucleotide sequence of SEQ ID NO:12, or a fragment, variant, or derivative thereof. In yet another preferred embodiment, the at least one synthetic nucleic acid sequence of the present invention has the nucleotide sequence of SEQ ID NO:13, or a fragment, variant, or derivative thereof. In still another preferred embodiment, the at least one synthetic nucleic acid sequence of the present invention has the nucleotide sequence of SEQ ID NO:14, or a fragment, variant, or derivative thereof. In a further embodiment, the at least one synthetic nucleic acid sequence of the present invention has the nucleotide sequence of SEQ ID NO:15, or a fragment, variant, or derivative thereof. In yet another preferred embodiment, the at least one synthetic nucleic acid sequence of the present invention has the nucleotide sequence of SEQ ID NO:16, or a fragment, variant, or derivative thereof.

The present invention further provides a kit for determining the presence or absence of SARS-associated coronavirus in a biological sample. The kit comprises at least one synthetic nucleic acid sequence and instructions for use. By way of example, the kit may comprise instructions for use of the synthetic nucleic acid sequence(s) in a polymerase chain reaction (PCR) reaction. Such instructions may include, without limitation, the conditions for performing the PCR reaction, such as annealing and extension temperatures, time periods, and number of cycles.

At least one of the synthetic nucleic acid sequences in the kit of the present invention is selected from the group consisting of: (a) a nucleic acid sequence comprising 10-30 consecutive nucleotides of at least one of the following: (i) the N gene region of the SARS-associated coronavirus genome; and (ii) the 3' non-coding region of the SARS-associated coronavirus genome; and (b) a nucleic acid sequence comprising 10-30 consecutive nucleotides of a nucleic acid sequence that is complementary to at least one of the following: (i) the N gene region of the SARS-associated coronavirus genome; and (ii) the 3' non-coding region of the SARS-associated coronavirus genome. In a preferred embodiment of the present invention, at least one of the synthetic nucleic acid sequences in the kit has a nucleotide sequence selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, and SEQ ID NO:16, and a fragment, variant, and derivative thereof.

The present invention also provides a kit for determining the presence or absence of SARS-associated coronavirus in a biological sample, comprising: (a) a primer set comprising at least two synthetic nucleic acid sequences for amplifying at least one nucleic acid sequence, wherein at least of one of the synthetic nucleic acid sequences in the kit is selected from the group consisting of: (i) a nucleic acid sequence comprising 10-30 consecutive nucleotides of at least one of the following: (A) the N gene region of the SARS-associated coronavirus genome; and (B) the 3' non-coding region of the SARS-associated coronavirus genome; and (ii) a nucleic acid sequence comprising 10-30 consecutive nucleotides of a nucleic acid sequence that is complementary to at least one of the following: (A) the N gene region of the SARS-associated coronavirus genome; and (B) the 3' non-coding region of the SARS-associated coronavirus genome; and (b) instructions for use. In one embodiment, the kit further comprises: (c) suitable reagents for a polymerase chain reaction (PCR); and (d) optionally, a positive and/or negative control for determining the presence or absence of SARS-associated coronavirus. Examples of suitable of PCR reagents include PCR reaction buffer, $Mg^{2+}$ (e.g., $MgCl_2$), dNTPs, DNA polymerases (such as reverse transcriptases and thermostable DNA polymerases (e.g., Taq-related DNA polymerases and Pfu-related DNA polymerases)), RNase, PCR reaction enhancers or inhibitors, PCR reaction monitoring agents (e.g., double-stranded DNA dye (such as SYBR® Green), TaqMan® probes, molecular beacons, and Scorpions®), and PCR-grade water.

In one embodiment of the present invention, two or more of the synthetic nucleic acid sequences in the primer set are selected from the group consisting of: (i) a nucleic acid sequence comprising 10-30 consecutive nucleotides of at least one of the following: (A) the N gene region of the SARS-associated coronavirus genome; and (B) the 3' non-coding region of the SARS-associated coronavirus genome; and (ii) a nucleic acid sequence comprising 10-30 consecutive nucleotides of a nucleic acid sequence that is complementary to at least one of the following: (A) the N gene region of the SARS-associated coronavirus genome; and (B) the 3' non-coding region of the SARS-associated coronavirus genome. In a preferred embodiment of the present invention, at least one synthetic nucleic acid sequences in the kit has a nucleotide sequence selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, and SEQ ID NO:16, and a fragment, variant, and derivative thereof.

The primers described herein will be particularly useful in a polymerase chain reaction (PCR) assay. PCR is a practical system for in vitro amplification of a DNA base sequence. For example, a PCR assay may use a heat-stable polymerase and two ~20-base primers: one complementary to the (+)-strand at one end of the sequence to be amplified, and the other complementary to the (−)-strand at the other end. Because the newly-synthesized DNA strands can subsequently serve as additional templates for the same primer sequences, successive rounds of primer annealing, strand elongation, and dissociation may produce rapid and highly-specific amplification of the desired sequence. PCR also may be used to detect the existence of a defined sequence in a DNA sample.

By way of example, a typical PCR assay might start with two synthetic oligonucleotide primers which are complementary to two regions of the target DNA (one for each strand) that is to be amplified. These may be added to the target DNA (that need not be pure) in the presence of excess deoxynucleotides (dNTPs) and a thermostable DNA polymerase (e.g., Taq polymerase). In a series (typically 20-40) of temperature cycles, the target DNA may be repeatedly denatured (~90° C.), annealed to the primers (typically at ~40-65° C.), and a daughter strand may be extended from the primers (typically at ~72° C.). As the daughter strands themselves act as templates for subsequent cycles, DNA fragments matching both primers are amplified exponentially, rather than linearly. The target DNA need be neither pure nor abundant; thus, PCR is widely used not only in research, but in clinical diagnostics.

The present invention further provides a method for determining the presence or absence of SARS-associated coronavirus in a biological sample, by: (a) contacting the biological sample with at least one synthetic nucleic acid sequence, under conditions suitable for amplification; and (b) determining the presence or absence of SARS-associated coronavirus in the biological sample. The synthetic nucleic acid sequence for use in the present invention is selected from the group consisting of: (i) a nucleic acid sequence comprising 10-30 consecutive nucleotides of at least one of the following: (A) the N gene region of the SARS-associated coronavirus genome; and (B) the 3' non-coding region of the SARS-associated coronavirus genome; and (ii) a nucleic acid sequence comprising 10-30 consecutive nucleotides of a nucleic acid sequence that is complementary to at least one of the following: (A) the N gene region of the SARS-associated coronavirus genome; and (B) the 3' non-coding region of the SARS-associated coronavirus genome.

In accordance with the method of the present invention, the biological sample may be obtained from any tissue of a subject, and may be removed by standard biopsy. In addition, the biological sample may be a bodily fluid, including cerebrospinal fluid, pericardial fluid, peritoneal fluid, saliva, serum, and urine. The subject may be any animal, particularly a mammal, including, without limitation, a cow, dog, human, monkey, mouse, pig, or rat. Preferably, the subject is a human. Furthermore, the subject may be known to have SARS, suspected of having SARS, or believed not to have SARS. In one embodiment of the present invention, the biological sample is obtained from a subject suspected of having SARS.

In a preferred embodiment of the present invention, the biological sample is mixed with the synthetic nucleic acid sequence and with suitable PCR reagents. A PCR reaction (e.g., PCR, reverse transcription PCR, real time PCR, and competitive PCR) is then performed, to amplify at least one nucleic acid sequence of the N gene region and/or the 3' non-coding region of the SARS-associated coronavirus genome. The product of the PCR reaction can be detected using standard methods known in the art, including, without limitation, electrophoresis (such as agarose gel electrophoresis, polyacrylamide gel electrophoresis, and capillary electrophoresis), chromatography (such as high performance liquid chromatography (HPLC) and gas chromatography (GC)), mass spectrometry (MS) (such as GC-MS), spectrophotometry (such as fluorescence spectrophotometry), immunoassays (such as ELISA), and melting-curve analysis. It is also within the confines of the present invention to use the inventors' primers to establish a synthetic standard for PCR and real time PCR assays that includes a restriction site to facilitate distinction of clinical isolates from synthetic RNAs used as positive controls.

The present invention is described in the following Examples, which are set forth to aid in the understanding of the invention, and should not be construed to limit in any way the scope of the invention as defined in the claims which follow thereafter.

EXAMPLES

Example 1

Development of PCR Primers

First-generation PCR assays for the SARS-associated coronavirus were previously established, as the initial genome sequence was obtained by degenerate PCR based on regions of conservation in the polymerase gene (Poutanen et al., Identification of Severe Acute Respiratory Syndrome in Canada. *N. Engl. J. Med.*, Apr. 10, 2003, e-pub; Drosten et al., Identification of a Novel Coronavirus in Patients with Severe Acute Respiratory Syndrome. *N. Engl. J. Med.*, Apr. 10, 2003, e-pub). Although these were useful, coronavirus biology indicates that higher sensitivity should be achieved by establishing PCR assays based on genetic signatures toward the 3' end of the coronavirus genome.

Accordingly, to facilitate development of these PCR assays, the inventors examined sequences deposited by other investigators at public sites and the Centers for Disease Control (CDC), as well as primary sequences of amplification products defined at Columbia University (Center for Immunopathogenesis and Infectious Diseases, or CIID) by degenerate PCR. A region comprising approximately 240 nucleotides (nt) within the 3' non-coding region (NCR) was chosen for standard and real-time PCR assays. Oligonucleotide primers for amplification and detection of this region were defined based on parameters implicated in primer performance, including melting temperature, 3'-terminal stability, internal stability, and propensity of potential primers to form stem loops or primer-dimers. Pilot assays were performed with clinical samples obtained from Mount Sinai Hospital (Toronto).

The NCR primer sets developed by the inventors are set forth below:

```
CIID-29398F
5'-ATg ACC ACA CAA ggC AgA Tgg      (SEQ ID NO:2)

CIID-29618R
5'-gCT CTC CCT AgC gTT ATT CAC TgT  (SEQ ID NO:3)

CIID-29405F
5'-CAC AAg gCA gAT ggg CTA TgT      (SEQ ID NO:4)

CIID-29619R
5'-gCT CTC CCT AgC gTT ATT CAC Tg   (SEQ ID NO:5)

CIID-29584T                         (SEQ ID NO:6)
5'-FAM-TTT CAT CgA ggC CAC gCg gAg TAC-T-TAMRA

CIID-29618-2R
5'-gCT CTC CCT AgC ATT ATT CAC TgT  (SEQ ID NO:7)

CIID-29426F
5'-AAA CgT TTT CgC AAT TCC gT       (SEQ ID NO:8)

CIID-29623R
5'-ggC AgC TCT CCC TAg CAT TAT TC   (SEQ ID NO:9)

CIID-29592T                         (SEQ ID NO:10)
5'-FAM-TCg ATC GTA CTC CGC GTG GCC T-T-TAMRA
```

The inventors have also developed additional primers that extend into, or are situated wholly within, the N gene region of the SARS-associated coronavirus. These are set forth below:

```
CIID-28506F
5'-Agg CAT CgT ATg ggT TgC A                          (SEQ ID NO:11)

CIID-28614R
5'-gAA gCC TTT Tgg CAA TgT TgT T                      (SEQ ID NO:12)

CIID-28529T
5'-FAM-Agg gAg CCT TgA ATA CAC CCA AAg ACC A-T-TAMRA  (SEQ ID NO:13)

CIID-28891F
5'-AAg CCT CgC CAA AAA CgT AC                         (SEQ ID NO:14)

CIID-29100R
5'-AAg TCA gCC ATg TTC CCg AA                         (SEQ ID NO:15)

CIID-29074T
5'-FAM-TCA CgC ATT ggC ATg gAA gTC ACA C-T-TAMRA      (SEQ ID NO:16)
```

Real-time PCR analysis performed using the inventors' primer set (SEQ ID NOs: 2-7) and a probe oligonucleotide yielded a profile consistent with sensitivity to 500 copies in approximately 100 ng of total RNA extracted postmortem from a SARS victim. NCR PCR performed in parallel with two polymerase gene assays reported by other investigators (from Canada and Germany) confirmed the anticipated higher sensitivity of NCR PCR (see Example 2). After one round of 45 cycles of amplification, NCR PCR yielded a signal equal to that yielded by the other assays that required nested amplification.

Example 2

Comparison of PCR Primers and Methods

The inventors compared their PCR primers (Example 1) and methods to those used previously in Canada and in Germany. The primers from Canada were obtained from the Canada Polymerase Primer Sets (Poutanen et al., Identification of Severe Acute Respiratory Syndrome in Canada. *N. Engl. J. Med.*, Apr. 10, 2003, e-pub). The primers from Germany were obtained from the Hamburg Polymerase Primer Sets, developed by the Bernhard Nocht Institute (BNI) (Drosten et al., Identification of a Novel Coronavirus in Patients with Severe Acute Respiratory Syndrome. *N. Engl. J. Med.*, Apr. 10, 2003, e-pub).

The primers from Canada are set forth below:

```
First PCR:
5'-CAg AgC CAT gCC TAA CAT g        (SEQ ID NO:17)

5'-AAT gTT TAC gCA ggT AAg Cg       (SEQ ID NO:18)

Second (Nested) PCR:
5'-TgT TAA CCA Ag Tgg AAC           (SEQ ID NO:19)

5'-CCT gTg TTg TAg ATT gCg          (SEQ ID NO:20)
```

The primers from Germany are set forth below:

```
First PCR:
BNIoutS2
5'-ATg AAT TAC CAA gTC AAT ggT TAC  (SEQ ID NO:21)

BNIoutAs
5'-CAT AAC CAg TCg gTA CAg CTA C    (SEQ ID NO:22)

Second (nested) PCR:
BNIinS
5'-gAA gCT ATT CgT CAC gTT Cg       (SEQ ID NO:23)

BNIinAs
5'-CTg TAg AAA ATC CTA gCT ggA g    (SEQ ID NO:24)
```

The results of the inventors' comparison are set forth in FIG. 2 (for lanes 1-4; first PCR) and described below:

Lane 1: CANADA Primers (Polymerase); First PCR; AmpliTaq conditions:

| | | | |
|---|---|---|---|
| cDNA | 1.0 µl | (Invitrogen Superscript II, random hexamers) | |
| Canada CoV F1 | 1.0 µl | (100 µM) | final conc. [2 µM] |
| Canada CoV R1 | 1.0 µl | (100 µM) | final conc. [2 µM] |
| dNTP | 1.0 µl | (25 mM) | final conc. [0.2 mM] |
| MgCl$_2$ | 5.0 µl | (25 mM) | final conc. [2.5 mM] |
| 10× buffer | 5.0 µl | | |
| AmpliTaq | 0.5 µl | | |
| H$_2$O | 35.5 µl | | |
| | 50 µl | | |

10 µl loaded onto 1.5% agarose gel in 1× TAE buffer
5 min, 92° C.; 45 cycles: 1 min, 94° C., 1 min, 50° C., 1 min, 68° C.; 5 min, 68° C.

Lane 2: BNI Primers (Polymerase); First PCR; AmpliTaq conditions:

| | | | |
|---|---|---|---|
| cDNA | 1.0 µl | (Invitrogen Superscript II, random hexamers) | |
| BNIoutAs | 0.2 µl | (100 µM) | final conc. [0.4 µM] |
| BNIoutS2 | 0.2 µl | (100 µM) | final conc. [0.4 µM] |
| dNTP | 1.0 µl | (25 mM) | final conc. [0.2 mM] |
| MgCl$_2$ | 3.0 µl | (25 mM) | final conc. [1.5 mM] |
| 10× buffer | 5.0 µl | | |
| AmpliTaq | 0.5 µl | | |
| H$_2$O | 39.1 µl | | |
| | 50 µl | | |

10 µl loaded onto 1.5% agarose gel in 1× TAE buffer
1 min, 94° C.; 10 cycles: 10 sec, 94° C., 10 sec, 60° C. (drop 1° C.), 20 sec, 72° C.; 40 cycles: 10 sec, 94° C., 10 sec, 56° C., 20 sec, 72° C., 5 min, 68° C.

Lane 3: Inventors' Primers; CIID-721F/CIID-2-964R; 30 cycles; AmpliTaq conditions:

| | | | |
|---|---|---|---|
| cDNA | 1.0 µl | (Invitrogen Superscript II, random hexamers) | |
| CIID-29398F | 1.0 µl | (100 µM) | final conc. [2 µM] |
| CIID-29618R | 1.0 µl | (100 µM) | final conc. [2 µM] |
| dNTP | 1.0 µl | (25 mM) | final conc. [0.2 mM] |
| MgCl$_2$ | 6.0 µl | (25 mM) | final conc. [3.0 mM] |
| 10× buffer | 5.0 µl | | |

-continued

| | | | |
|---|---|---|---|
| AmpliTaq | 0.5 µl | | |
| H₂O | 34.5 µl | | |
| | 50 µl | | |

10 µl loaded onto 1.5% agarose gel in 1× TAE buffer
5 min, 92° C.; 30 cycles: 1 min, 94° C., 1 min, 56° C.,
1 min, 68° C.; 5 min, 68° C.

Lane 4: Inventors' Primers, CIID-721F/CIID-2-964R;
45 cycles; AmpliTaq conditions:

| | | | |
|---|---|---|---|
| cDNA | 1.0 µl | (Invitrogen Superscript II, random hexamers) | |
| CIID-29398F | 1.0 µl | (100 µM) | final conc. [2 µM] |
| CIID-29618R | 1.0 µl | (100 µM) | final conc. [2 µM] |
| dNTP | 1.0 µl | (25 mM) | final conc. [0.2 mM] |
| MgCl₂ | 6.0 µl | (25 mM) | final conc. [3.0 mM] |
| 10× buffer | 5.0 µl | | |
| AmpliTaq | 0.5 µl | | |
| H₂O | 34.5 µl | | |
| | 50 µl | | |

10 µl loaded onto 1.5% agarose gel in 1× TAE buffer
5 min, 92° C.; 45 cycles: 1 min, 94° C., 1 min, 56° C.,
1 min, 68° C.; 5 min, 68° C.

Lane 6: BNI Primers; Second PCR

| | | | |
|---|---|---|---|
| DNA 1$^{st}$ amp. | 1.0 µl | (Invitrogen Superscript II, random hexamers) | |
| BNIinAs | 0.2 µl | (100 µM) | final conc. [0.4 µM] |
| BNIinS2 | 0.2 µl | (100 µM) | final conc. [0.4 µM] |
| dNTP | 1.0 µl | (25 mM) | final conc. [0.2 mM] |
| MgCl₂ | 5.0 µl | (25 mM) | final conc. [1.5 mM] |
| 10× buffer | 5.0 µl | | |
| AmpliTaq | 0.5 µl | | |
| H₂O | 37.1 µl | | |
| | 50 µl | | |

5 µl loaded onto 1.5% agarose gel in 1× TAE buffer
1 min, 94° C.; 10 cycles: 10 sec, 94° C., 10 sec, 60° C., 20 sec,
72° C.; 25 cycles: 10 sec,
94° C., 10 sec, 56° C., 20 sec, 72° C., 5 min, 68° C.

Lane 7: CANADA Primers; Second PCR

| | | | |
|---|---|---|---|
| DNA 1$^{st}$ amp. | 1.0 µl | (Invitrogen Superscript II, random hexamers) | |
| Canada CoV F2 | 1.0 µl | (100 µM) | final conc. [2 µM] |
| Canada CoV R2 | 1.0 µl | (100 µM) | final conc. [2 µM] |
| dNTP | 1.0 µl | (25 mM) | final conc. [0.2 mM] |
| MgCl₂ | 4.0 µl | (25 mM) | final conc. [2.0 mM] |
| 10× buffer | 5.0 µl | | |
| AmpliTaq | 0.5 µl | | |
| H₂O | 36.5 µl | | |
| | 50 µl | | |

10 µl loaded onto 1.5% agarose gel in 1× TAE buffer
5 min, 92° C.; 45 cycles: 1 min, 94° C., 1 min, 50° C.,
1 min, 68° C.; 5 min, 68° C.

As the protocols demonstrate, only the inventors' PCR method reveals viral sequences without a requirement for nesting.

Example 3

Real Time PCR Assay of Samples from Subjects Diagnosed with Probable SARS

The inventors used the real time PCR assay of the present invention in a survey of more than 700 samples from persons diagnosed with probable SARS during the 2003 epidemic in Beijing, China.

Primers and probe were selected in the N (nucleocapsid protein) gene region at the 3' end of the SARS-CoV genome by using Primer Express Software (PE Applied Biosystems, Foster City, Calif.). The primer set used was: Taq-772F 5'-AAGCCTCGCCAAAAACGTAC (SEQ ID NO:14) (forward) and Taq-1000R 5'-AAGTCAGCCATGTTCCCGAA (SEQ ID NO:15) (reverse), Taq-955T 5'-FAM-TCACGCAT-TGGCATGGAAGTCA-CAC-T-TAMRA (SEQ ID NO:16) (probe), labeled with the reporter FAM (6-carboxyfluorescein) and the quencher TAMRA (6-carboxytetramethylrhodamine) (TIB Molbiol, Berlin, Germany).

A calibration standard was generated by PCR amplification of a 1,277-hp fragment composing part of the N open reading frame (ORF) and the 3' noncoding region (Co-STND-U275, 5'-CCCGACGAGTTCGTGGTGGTG (SEQ ID NO:25); Co-STND-L1529, 5'-GCGTTACACATT-AGGGCTCTTC CATA) (SEQ ID NO:26). The product was cloned into vector pGEM-Teasy (Invitrogen, Carlsbad, Calif.), and serial dilutions of linearized plasmid were used to optimize the assay. RNA standards were generated by in vitro transcription of linearized plasmid DNA using a mMES-SAGE mMACHINE T7 kit as recommended by the manufacturer (Ambion, Austin, Tex.). A portion of the construct (nucleotides 682-1105 of the N ORF) was modified through site-directed mutagenesis, to distinguish plasmid-derived products from authentic products in diagnostic applications. Mutations introduced were an A to G change at position 845 of the N ORE and an A to C change at position 866, creating a unique ApaI restriction site.

Detection of live virus was assessed by using supernatant from virus-infected Vero E6 cells (isolate BJO1; 4th passage; $10^8$ TCID$_{50}$/mL) tenfold diluted to $10^{-12}$ in tissue culture media. RNA from 140-µL aliquots of each dilution was extracted and resuspended in 60 µL of DEPC-treated water for reverse transcription (9 µL RNA/20-µL reaction) and PCR (5 µL/assay). 20 µL of each virus dilution were spiked into 180 µL of clarified supernatant of a fecal preparation to simulate clinical specimens, and RNA from 140-µL aliquots was extracted and processed as above.

Clinical materials, including 326 fecal and 426 whole blood samples, were collected from Chaoyang Hospital, 301 Hospital, You'an Hospital, and Xuanwu Hospital, Beijing. All persons had a diagnosis of probable SARS according to World Health Organization (WHO) criteria. For analysis of fecal samples, 1 g of stool was suspended in 1 mL of phosphate-buffered saline, mixed vigorously, and centrifuged for 10 min at 3,000 g, 4° C. Supernatant was collected for RNA extraction and PCR analysis. For analysis of blood samples, whole blood was fractionated using Ficoll Paque (Amersham Pharmacia, England). Plasma was collected and immunoglobulin (Ig) G and IgM levels were determined with an ELISA kit from the Beijing Genomics Institute (Beijing, China). Peripheral blood mononuclear cells were collected and RNA extracted by using the QiaAmp Viral RNA Mini Kit (Qiagen, Germany). Nine microliters total RNA was reverse transcribed (Superscript II Transcriptase, Invitrogen), and 2 µL of cDNA subjected to PCR by using a TaqMan Universal Master Mix kit (PE Applied Biosystems) on an ABI Prism 7900 HT sequence detector (PE Applied Biosystems). Thermocycling conditions were: 2 min 50° C. (AmpErase UNG), 10 min 95° C. (polymerase activation); 45 cycles of 15s 95° C. denaturation, and 1 min 60° C. annealing/extension.

A standard curve of plasmid concentration versus threshold cycle was generated with a cloned version of the 3' terminal portion of the viral genome. A correlation coefficient (r2) of 0.9913 showed a linear relationship between threshold cycle (Ct) and plasmid concentration (0-$10^5$ copies) (FIG. 4A). The detection limit for plasmid DNA was ≦5 copies per assay (Ct=42.66). A linear relationship was consistently obtained for input loads of $10^1$-$10^5$ copies per assay.

Standards for RT-PCR were generated by in vitro transcription of RNA from linearized plasmid template with T7 polymerase. Logarithmic dilutions of the synthesized RNA yielded results comparable to the DNA standards (r2=0.9950; FIG. 4B).

Supernatant from infected Vero E6 cells was serially diluted to determine the detection limit for live virus. Analysis of RNA extracted from logarithmic dilutions indicated a detection threshold of 0.0005 $TCID_{50}$ ($10^9$ dilution; 0.1 $TCID_{50}$/mL; 0.0005 $TCID_{50}$ per assay well). The threshold for detection of SARS-CoV in spiked fecal samples was 0.005 $TCID_{50}$ ($10^{-7}$ dilution; 1 $TCID_{50}$ /mL: 0.005 $TCID_{50}$ per assay well).

Figure 5A:
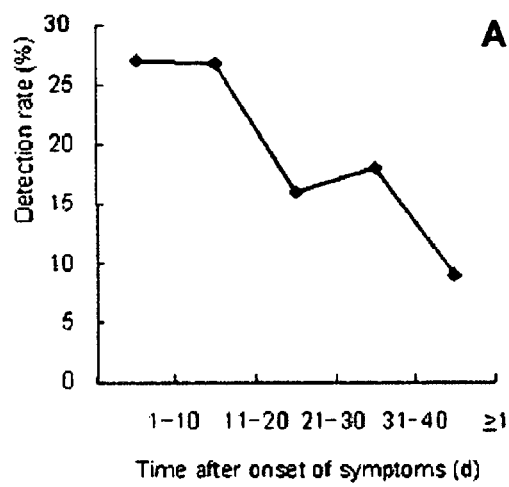
FIG. 5(A) shows real-time polymerase chain reaction (PCR) analysis of fecal samples.
Figure 5B:
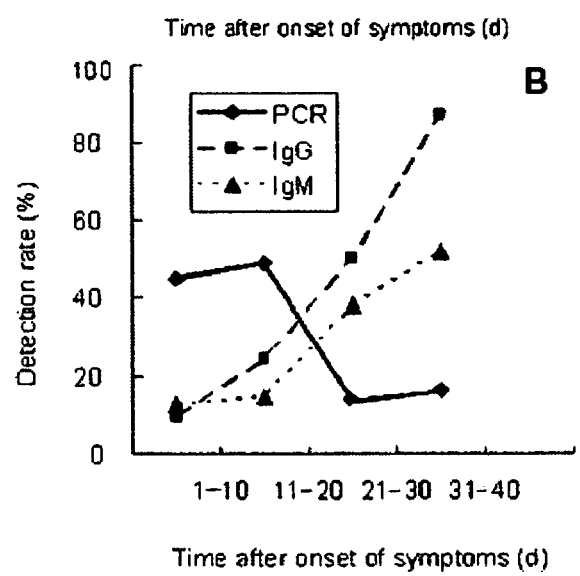
FIG. 5(B) shows real-time PCR, immunoglobulin (Ig) M and IgG analysis of blood samples.

Materials from persons who had probable SARS included 326 fecal samples and 426 blood samples. Control specimens collected during the outbreak from healthy persons included 16 fecal samples and 82 blood samples. The detection rate in fecal samples was 27% during the first 20 days after onset of symptoms (Table I, FIG. 5A). In the 20 days that followed, the detection rate declined to 16% to 18%, but even after >40 days, 9% of samples gave a positive reading. A similar time was observed in the analysis of blood samples; however, a higher the detection rate of 45% to 49% was obtained (note that only 11 of the samples were matched for blood and feces). During the first 20 days after onset of symptoms, the detection rate of RT-PCR in blood was significantly higher than that for IgM (10%-24%) or IgG antibodies (13%-15%) (Table I, FIG. 5B). Twenty-one to 40 days after onset of symptoms, serologic findings were more frequently positive than RT-PCR.

ology of acute respiratory illness in patients with suspected severe acute respiratory syndrome (SARS) in Switzerland. *Swiss Med. Wkly.* 2003, 133:400-1). However, confidence in the clinical criteria is enhanced by an 87% seropositivity in samples taken 310 days after onset of symptoms.

Current real-time RT-PCR assays allow sensitive detection of SARS-CoV nucleic acid in clinical specimens by targeting N gene sequence, as shown here, or pot gene sequence (Drosten, et al. Identification of a novel coronavirus in patients with severe acute respiratory syndrome. *N. Eng. J. Med.* 2003, 348:1967-76; Wu, et al. Establishment of a fluorescent polymerase chain reaction method for the detection of the SARS-associated coronavirus an its clinical application. *Chin. Med. J.* 2003, 116:988-90; Poon, et al. Early diagnosis of SARS coronavirus infection by real time Kf-PCR. *J. Clin. Virol.* 2003, 28:233-8; Yam, et al. Evaluation of reverse transcription-PCR assays for rapid diagnosis of severe acute respiratory syndrome associated with a novel coronavirus. *J. Clin. Microbiol.* 2003, 41:4521-4; Mazzulli, et al. Severe acute respiratory syndrome-associated coronavirus in lung tissue. *Emerg. Infect. Dis.* 2004, 10:20-4). A major advantage to real-time PCR platforms is that amplification and analysis are completed in a closed system. Thus, the risk of contamination, which can confound conventional (frequently nested) RT-PCR protocols (Poutanen, et al. Identification of severe acute respiratory syndrome in Canada. *N. Eng. J. Med.* 2003, 348:1995-2005; Drosten, et al. Identification of a novel coronavirus in patients with severe acute respiratory syndrome. *N. Eng. J. Med* 2003, 348:1967-76; Zhou, et al. Identification and molecular cloning and sequence analysis of a novel coronavirus from patients with SARS by RT-PCR. *Zhonghua Shi Yan He Lin Chuang Bing Du Xue Za Zhi* 2003, 17:137-9), is

TABLE I

Summary of clinical samples[a]

| Specimens | Total patients | 1-10 d | | 11-20 d | | 21-30 d | | 31-40 d | | >40 d | |
|---|---|---|---|---|---|---|---|---|---|---|---|
| | | pos | neg | pos | neg | pos | neg | pos | neg | pos | neg |
| Feces PCR | 326 | 10 | 27 | 19 | 52 | 12 | 65 | 12 | 55 | 7 | 67 |
| Blood PCR | 426 | 28 | 34 | 20 | 21 | 22 | 143 | 26 | 132 | NA | NA |
| Blood 1 gG | 426 | 6 | 56 | 10 | 31 | 82 | 83 | 138 | 20 | NA | NA |
| Blood 1 gM | 426 | 8 | 54 | 6 | 35 | 63 | 102 | 82 | 76 | NA | NA |

[a]pos, positive;
neg, negative;
PCR, polymerase chain reaction;
Ig, immunoglobulin;
NA, not available.

Of the 16 fecal and 82 blood samples obtained from healthy persons, one blood sample yielded a positive result in RT-PCR (confirmed by repeated assays). Because the sample was collected during the outbreak, it may represent a true infection in a person who was not yet symptomatic or who did not have classical symptoms.

The inventors also analyzed 180 sputum and 76 throat-washing samples from an unrelated cohort of persons with a diagnosis of probable SARS, for which the time after onset of symptoms had not been reported. The RT-PCR detection rate obtained in these samples was 63% for, and 15% for sputum samples, throat washing samples.

It was not possible during the Beijing outbreak to obtain clinical materials in a prospective serial fashion from a defined SARS-CoV-infected patient cohort. Thus, some samples represent persons with respiratory symptoms caused by pathogens other than SARS-CoV (Kaiser, et al. Viral aetimarkedly reduced. Whether different positivity rates reported for various SARS-CoV assays (Wu, et al. Establishment of a fluorescent polymerase chain reaction method for the detection of the SARS-associated coronavirus an its clinical application. *Chin. Med. J.* 2003, 116:988-90; Poon, et al. Early diagnosis of SARS coronavirus infection by real time Kf-PCR. *J. Clin. Virol.* 2003, 28:233-8; Yam, et al. Evaluation of reverse transcription-PCR assays for rapid diagnosis of severe acute respiratory syndrome associated with a novel coronavirus. *J. Clin. Microbiol.* 2003, 41:4521-4; Ren, et al. Detection of SARS-CoV RNA in stool samples of SARS patients by nest Rf-PCR and its clinical value. *Zhongguo Yi Xue Ke Xue Yuan Xue Bao* 2003, 25:368-71) reflect true differences in assay performance, or merely differences in specimen type or differences in sample preparation (Poon, et al. *J. Clin. Virol.* 2003, 28:233-8), will only become apparent after comparative quality control tests using identical samples in the various assays and laboratories. Using calibrated DNA and RNA standards, the inventors achieved comparable results with the assay reported here in laboratories in New York and Beijing.

RNA integrity is a critical determinant of sensitivity in RT-PCR SARS-CoV assays. Samples were not collected at clinical sites with the objective of nucleic acid analysis. Additionally, protocols adopted by the various hospitals for sample collection, handling, and storage were not uniform. Nonetheless, RT-PCR analysis resulted in consistent results for all 11 cases of matching feces and blood samples. Furthermore, all blood samples seropositive during the first 20 days after onset of symptoms were also positive in RT-PCR. Of the 48 RT-PCR positive samples collected 21-40 clays after onset of symptoms, 45 were also seropositive.

RT-PCR analysis of blood was a less sensitive index of infection than immunologic assays at later time points (21-40 days after onset of symptoms). However, 16% of blood samples and 18% of fecal samples contained SARS-CoV RNA >31-40 days after onset of symptoms. A similar duration of persistence of SARS sequences in stool has been observed by Ren, et al (Ren, et al. *Zhongguo Yi Xue Ke Xue Yuan Xue Bao* 2003, 25:368-71). Whether infectious virus is present at these later time points remains to be determined; nonetheless, these findings indicate that long-term monitoring may he required to control dissemination of disease.

While the foregoing invention has been described in some detail for purposes of clarity and understanding, it will be appreciated by one skilled in the art, from a reading of the disclosure, that various changes in form and detail can be made without departing from the true scope of the invention in the appended claims.

SEQUENCE LISTING

```
<160> NUMBER OF SEQ ID NOS: 16

<210> SEQ ID NO 1
<211> LENGTH: 1136
<212> TYPE: DNA
<213> ORGANISM: artificial sequence
<220> FEATURE:
<223> OTHER INFORMATION: synthetic nucleic acid sequence that includes
      the 3' non-coding region of the SARS-associated coronavirus genome
      and a portion of the N gene of the SARS-associated coronavirus
      genome

<400> SEQUENCE: 1
aggcatcgta tgggttgcaa ctgagggagc cttgaataca cccaaagacc acattggcac        60
ccgcaatcct aataacaatg ctgccaccgt gctacaactt cctcaaggaa caacattgcc       120
aaaaggcttc tacgcagagg gaagcagagg cggcagtcaa gcctcttctc gctcctcatc       180
acgtagtcgc ggtaattcaa gaaattcaac tcctggcagc agtaggggaa attctcctgc       240
tcgaatggct agcggaggtg gtgaaactgc cctcgcgcta ttgctgctag acagattgaa       300
ccagcttgag agcaaagttt ctggtaaagg ccaacaacaa caaggccaaa ctgtcactaa       360
gaaatctgct gctgaggcat ctaaaaagcc tcgccaaaaa cgtactgcca caaaacagta       420
caacgtcact caagcatttg ggagacgtgg tccagaacaa acccaaggaa atttcgggga       480
ccaagaccta atcagacaag gaactgatta caaacattgg ccgcaaattg cacaatttgc       540
tccaagtgcc tctgcattct ttggaatgtc acgcattggc atggaagtca caccttcggg       600
aacatggctg acttatcatg gagccattaa attggatgac aaagatccac aattcaaaga       660
caacgtcata ctgctgaaca agcacattga cgcatacaaa acattcccac caacagagcc       720
taaaaaggac aaaagaaaa agactgatga agctcagcct tgccgcaga gacaaaagaa       780 gcagcccact gtgactcttc ttcctgcggc tgacatggat gatttctcca gacaacttca       840
aaattccatg agtggagctt ctgctgattc aactcaggca taaacactca tgatgaccac       900
acaaggcaga tgggctatgt aaacgttttc gcaattccgt ttacgataca tagtctactc       960
ttgtgcagaa tgaattctcg taactaaaca gcacaagtag gtttagttaa ctttaatctc      1020
acatagcaat ctttaatcaa tgtgtaacat tagggaggac ttgaaagagc caccacattt      1080
tcatcgaggc cacgcggagt acgatcgagg gtacagtgaa taatgctagg gagagc         1136

<210> SEQ ID NO 2
```

```
<211> LENGTH: 21
<212> TYPE: DNA
<213> ORGANISM: artificial sequence
<220> FEATURE:
<223> OTHER INFORMATION: primer

<400> SEQUENCE: 2
atgaccacac aaggcagatg g                                           21

<210> SEQ ID NO 3
<211> LENGTH: 24
<212> TYPE: DNA
<213> ORGANISM: artificial sequence
<220> FEATURE:
<223> OTHER INFORMATION: primer

<400> SEQUENCE: 3
gctctcccta gcgttattca ctgt                                        24

<210> SEQ ID NO 4
<211> LENGTH: 21
<212> TYPE: DNA
<213> ORGANISM: artificial sequence
<220> FEATURE:
<223> OTHER INFORMATION: primer

<400> SEQUENCE: 4
cacaaggcag atgggctatg t                                           21

<210> SEQ ID NO 5
<211> LENGTH: 23
<212> TYPE: DNA
<213> ORGANISM: artificial sequence
<220> FEATURE:
<223> OTHER INFORMATION: primer

<400> SEQUENCE: 5
gctctcccta gcgttattca ctg                                         23

<210> SEQ ID NO 6
<211> LENGTH: 27
<212> TYPE: DNA
<213> ORGANISM: artificial sequence
<220> FEATURE:
<223> OTHER INFORMATION: primer

<400> SEQUENCE: 6
tttcatcgag gccacgcgga gtactta                                     27

<210> SEQ ID NO 7
<211> LENGTH: 24
<212> TYPE: DNA
<213> ORGANISM: artificial sequence
<220> FEATURE:
<223> OTHER INFORMATION: primer

<400> SEQUENCE: 7
gctctcccta gcattattca ctgt                                        24

<210> SEQ ID NO 8
<211> LENGTH: 20
<212> TYPE: DNA
<213> ORGANISM: artificial sequence
<220> FEATURE:
<223> OTHER INFORMATION: primer

<400> SEQUENCE: 8
```
aaacgttttc gcaattccgt                                        20

<210> SEQ ID NO 9
<211> LENGTH: 23
<212> TYPE: DNA
<213> ORGANISM: artificial sequence
<220> FEATURE:
<223> OTHER INFORMATION: primer

<400> SEQUENCE: 9
ggcagctctc cctagcatta ttc                                    23

<210> SEQ ID NO 10
<211> LENGTH: 25
<212> TYPE: DNA
<213> ORGANISM: artificial sequence
<220> FEATURE:
<223> OTHER INFORMATION: primer

<400> SEQUENCE: 10
tcgatcgtac tccgcgtggc cttta                                  25

<210> SEQ ID NO 11
<211> LENGTH: 19
<212> TYPE: DNA
<213> ORGANISM: artificial sequence
<220> FEATURE:
<223> OTHER INFORMATION: primer

<400> SEQUENCE: 11
aggcatcgta tgggttgca                                         19

<210> SEQ ID NO 12
<211> LENGTH: 22
<212> TYPE: DNA
<213> ORGANISM: artificial sequence
<220> FEATURE:
<223> OTHER INFORMATION: primer

<400> SEQUENCE: 12
gaagcctttt ggcaatgttg tt                                     22

<210> SEQ ID NO 13
<211> LENGTH: 31
<212> TYPE: DNA
<213> ORGANISM: artificial sequence
<220> FEATURE:
<223> OTHER INFORMATION: primer

<400> SEQUENCE: 13
agggagcctt gaatacaccc aaagaccatt a                           31

<210> SEQ ID NO 14
<211> LENGTH: 20
<212> TYPE: DNA
<213> ORGANISM: artificial sequence
<220> FEATURE:
<223> OTHER INFORMATION: primer

<400> SEQUENCE: 14
aagcctcgcc aaaaacgtac                                        20

<210> SEQ ID NO 15
<211> LENGTH: 20
<212> TYPE: DNA

-continued

```
<213> ORGANISM: artificial sequence
<220> FEATURE:
<223> OTHER INFORMATION: primer

<400> SEQUENCE: 15
aagtcagcca tgttcccgaa                                           20

<210> SEQ ID NO 16
<211> LENGTH: 28
<212> TYPE: DNA
<213> ORGANISM: artificial sequence
<220> FEATURE:
<223> OTHER INFORMATION: primer

<400> SEQUENCE: 16
tcacgcattg gcatggaagt cacactta                                  28
```

What is claimed is:

1. A synthetic nucleic acid which has a sequence consisting of from 19 to 30 consecutive nucleotides of SEQ ID NO: 43.

2. A composition comprising one or more of the synthetic nucleic acid of claim 1.

3. A method for determining the presence or absence of SARS-associated corona virus in a biological sample, the method comprising:
   a) contacting nucleic acid from a biological sample with at least one primer which is a nucleic acid of claim 1,
   b) subjecting the nucleic acid and the primer to amplification conditions, and
   c) determining the presence or absence of amplification product, wherein the presence of amplification product indicates the presence of RNA associated with corona virus in the sample.

4. A synthetic nucleic acid which has a sequence consisting of from 19 to 30 consecutive nucleotides of a nucleic acid sequence that is complementary to SEQ ID NO: 43.

5. A composition comprising one or more of the synthetic nucleic acid of claim 4.

6. A method for determining the presence or absence of SARS-associated corona virus in a biological sample, the method comprising:
   a) contacting nucleic acid from a biological sample with at least one primer which is a nucleic acid of claim 4,
   b) subjecting the nucleic acid and the primer to amplification conditions, and
   c) determining the presence or absence of amplification product, wherein the presence of amplification product indicates the presence of RNA associated with corona virus in the sample.

7. A primer set for determining the presence or absence of SARS-associated corona virus in a biological sample, wherein the primer set comprises at least one synthetic nucleic acid sequence selected from the group consisting of:
   (a) a synthetic nucleic acid sequence consisting of from 19 to 30 consecutive nucleotides of SEQ ID NO: 43; and
   (b) a synthetic nucleic acid sequence consisting of from 19 to 30 consecutive nucleotides of a nucleic acid sequence that is complementary to SEQ ID NO: 43.

8. The primer set of claim 7, wherein the at least one synthetic nucleic acid sequence has a nucleotide sequence selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

9. The primer set of claim 8, wherein the at least one synthetic nucleic acid sequence has the nucleotide sequence of SEQ ID NO: 2.

10. The primer set of claim 8, wherein the at least one synthetic nucleic acid sequence has the nucleotide sequence of SEQ ID NO: 3.

11. The primer set of claim 8, wherein the at least one synthetic nucleic acid sequence has the nucleotide sequence of SEQ ID NO: 4.

12. The primer set of claim 8, wherein the at least one synthetic nucleic acid sequence has the nucleotide sequence of SEQ ID NO: 5.

13. The primer set of claim 8, wherein the at least one synthetic nucleic acid sequence has the nucleotide sequence of SEQ ID NO: 6.

14. The primer set of claim 8, wherein the at least one synthetic nucleic acid sequence has the nucleotide sequence of SEQ ID NO: 7.

15. The primer set of claim 8, wherein the at least one synthetic nucleic acid sequence has the nucleotide sequence of SEQ ID NO: 8.

16. The primer set of claim 8, wherein the at least one synthetic nucleic acid sequence has the nucleotide sequence of SEQ ID NO: 9.

17. The primer set of claim 8, wherein the at least one synthetic nucleic acid sequence has the nucleotide sequence of SEQ ID NO: 10.

18. The primer set of claim 8, wherein the at least one synthetic nucleic acid sequence has the nucleotide sequence of SEQ ID NO: 11.

19. The primer set of claim 8, wherein the at least one synthetic nucleic acid sequence has the nucleotide sequence of SEQ ID NO: 12.

20. The primer set of claim 8, wherein the at least one synthetic nucleic acid sequence has the nucleotide sequence of SEQ ID NO: 13.

21. The primer set of claim 8, wherein the at least one synthetic nucleic acid sequence has the nucleotide sequence of SEQ ID NO: 11.

22. The primer set of claim 8, wherein the at least one synthetic nucleic acid sequence has the nucleotide sequence of SEQ ID NO: 15.

23. The primer set of claim 8, wherein the at least one synthetic nucleic acid sequence has the nucleotide sequence of SEQ ID NO: 16.

24. A composition comprising the primer set of claim 7.

25. A method for determining the presence or absence of SARS-associated corona virus in a biological sample the method comprising:
   a) contacting nucleic acid from a biological sample with primer set of claim 7,
   b) subjecting the nucleic acid and the primers to amplification conditions, and
   c) determining the presence or absence of amplification product, wherein the presence of amplification product indicates the presence of RNA associated with corona virus in the sample.

26. A kit for determining the presence or absence of SARS-associated corona virus in a biological sample, comprising at least one of the synthetic nucleic acids of claim 1 or 4.

27. The kit of claim 26, wherein the at least one synthetic nucleic acid sequence has a nucleotide sequence selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

28. A kit for determining the presence or absence of SARS-associated corona virus in a biological sample, comprising:
   a primer set comprising at least two synthetic nucleic acid sequences, wherein at least one of the at least two synthetic nucleic acid sequences is selected from the synthetic nucleic acid of claims 1 or 4.

29. The kit of claim 28, wherein the at least one nucleic acid sequence has a nucleotide sequence selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

30. The kit of claim 28, further comprising:
   (c) suitable PCR reagents; and
   (d) optionally, a positive and/or negative control for determining the presence or absence of SARS-associated corona virus.

31. The kit of claim 30, wherein the PCR reagents include a thermostable DNA polymerase and dNTP solutions.

32. The method of any one of claims 3, or 25, wherein the biological sample is obtained from a subject suspected of having SARS.

33. A composition comprising a mixture of at least two synthetic nucleotides of claim 1 or 4.

34. A synthetic nucleic acid of any one of claims 1, 4 or 7, wherein the synthetic nucleic acid is linked to a fluorescent reporter.

35. The method of any one of claims 3, 6 or 25, further comprising a synthetic nucleic acid linked to a fluorescent reporter.

36. The methods of any one of claims 3, 6 or 25, wherein the presence of amplified nucleic acid in step c) can be determined by separating and visualizing the amplified nucleic acids by electrophoresis to obtain separate products, or by determining the amount of fluorescence after at least one amplification cycle.

37. A synthetic nucleic acid which has a sequence consisting of from 19 to 28 consecutive nucleotides of SEQ ID NO: 43.

38. A synthetic nucleic acid which has a sequence consisting of from 19 to 28 consecutive nucleotides of a nucleic acid sequence that is complementary to SEQ ID NO: 43.

39. A synthetic nucleic acid which has a sequence consisting of from 19 to 30 consecutive nucleotides of N-gene region or 3' non-coding region of SARS-associated coronavirus genome.

40. A synthetic nucleic acid which has a sequence consisting of from 19 to 30 consecutive nucleotides of a nucleic acid sequence that is complementary to N-gene region or 3' non-coding region of SARS-associated coronavirus genome.

41. A synthetic nucleic acid which has the sequence consisting of SEQ ID NO: 2.

42. A synthetic nucleic acid which has a sequence consisting of SEQ ID NO: 3.

43. A synthetic nucleic acid which has a sequence consisting of SEQ ID NO: 4.

44. A synthetic nucleic acid which has a sequence consisting of SEQ ID NO: 5.

45. A synthetic nucleic acid which has a sequence consisting of SEQ ID NO: 6.

46. A synthetic nucleic acid which has a sequence consisting of SEQ ID NO: 7.

47. A synthetic nucleic acid which has a sequence consisting of SEQ ID NO: 8.

48. A synthetic nucleic acid which has a sequence consisting of SEQ ID NO: 9.

49. A synthetic nucleic acid which has a sequence consisting of SEQ ID NO: 10.

50. A synthetic nucleic acid which has a sequence consisting of SEQ ID NO: 11.

51. A synthetic nucleic acid which has a sequence consisting of SEQ ID NO: 12.

52. A synthetic nucleic acid which has a sequence consisting of SEQ ID NO: 13.

53. A synthetic nucleic acid which has a sequence consisting of SEQ ID NO: 14.

54. A synthetic nucleic acid which has a sequence consisting of SEQ ID NO: 15.

55. A synthetic nucleic acid which has a sequence consisting of SEQ ID NO: 16.

56. The synthetic nucleic acid of any one of claims 45, 49, 52 or 55, wherein the synthetic nucleic acid is linked to fluorescent reporter.

57. A method for determining the presence or absence of SARS-associated corona virus in a sample, the method comprising:
   a) contacting nucleic acid from a sample with at least one primer which is the nucleic acid of SEQ ID NO: 2,
   b) subjecting the nucleic acid and the primer to amplification conditions, and
   c) determining the presence or absence of amplification product.

58. A method for determining the presence or absence of SARS-associated corona virus in a sample, the method comprising:
   a) contacting nucleic acid from a sample with at least one primer which is a nucleic acid of SEQ ID NO: 3,
   b) subjecting the nucleic acid and the primer to amplification conditions, and
   c) determining the presence or absence of amplification product.

59. A method for determining the presence or absence of SARS-associated corona virus in a sample, the method comprising:
   a) contacting nucleic acid from a sample with at least one primer which is a nucleic acid of SEQ ID NO: 4, b) subjecting the nucleic acid and the primer to amplification conditions, and c) determining the presence or absence of amplification product.

60. A method for determining the presence or absence of SARS-associated corona virus in a sample, the method comprising:

a) contacting nucleic acid from a sample with at least one primer which is a nucleic acid of SEQ ID NO: 5, b) subjecting the nucleic acid and the primer to amplification conditions, and c) determining the presence or absence of amplification product.

61. A method for determining the presence or absence of SARS-associated corona virus in a sample, the method comprising:

a) contacting nucleic acid from a sample with at least one primer which is a nucleic acid of SEQ ID NO: 6, b) subjecting the nucleic acid and the primer to amplification conditions, and c) determining the presence or absence of amplification product.

62. A method for determining the presence or absence of SARS-associated corona virus in a sample, the method comprising:

a) contacting nucleic acid from a sample with at least one primer which is a nucleic acid of SEQ IDNO: 7, b) subjecting the nucleic acid and the primer to amplification conditions, and c) determining the presence or absence of amplification product.

63. A method for determining the presence or absence of SARS-associated corona virus in a sample, the method comprising:

a) contacting nucleic acid from a sample with at least one primer which is a nucleic acid of SEQ ID NO: 8, b) subjecting the nucleic acid and the primer to amplification conditions, and c) determining the presence or absence of amplification product.

64. A method for determining the presence or absence of SARS-associated corona virus in a sample, the method comprising:

a) contacting nucleic acid from a sample with at least one primer which is a nucleic acid of SEQ ID NO: 9, b) subjecting the nucleic acid and the primer to amplification conditions, and c) determining the presence or absence of amplification product.

65. A method for determining the presence or absence of SARS-associated corona virus in a sample, the method comprising:

a) contacting nucleic acid from a sample with at least one primer which is a nucleic acid of SEQ ID NO: 10, b) subjecting the nucleic acid and the primer to amplification conditions, and c) determining the presence or absence of amplification product.

66. A method for determining the presence or absence of SARS-associated corona virus in a sample, the method comprising:

a) contacting nucleic acid from a sample with at least one primer which is a nucleic acid of SEQ ID NO: 11, b) subjecting the nucleic acid and the primer to amplification conditions, and c) determining the presence or absence of amplification product.

67. A method for determining the presence or absence of SARS-associated corona virus in a sample, the method comprising:

a) contacting nucleic acid from a sample with at least one primer which is a nucleic acid of SEQ ID NO: 12, b) subjecting the nucleic acid and the primer to amplification conditions, and c) determining the presence or absence of amplification product.

68. A method for determining the presence or absence of SARS-associated corona virus in a sample, the method comprising:

a) contacting nucleic acid from a sample with at least one primer which is a nucleic acid of SEQ ID NO: 13, b) subjecting the nucleic acid and the primer to amplification conditions, and c) determining the presence or absence of amplification product.

69. A method for determining the presence or absence of SARS-associated corona virus in a sample, the method comprising:

a) contacting nucleic acid from a sample with at least one primer which is a nucleic acid of SEQ ID NO: 14, b) subjecting the nucleic acid and the primer to amplification conditions, and c) determining the presence or absence of amplification product.

70. A method for determining the presence or absence of SARS-associated corona virus in a sample, the method comprising:

a) contacting nucleic acid from a sample with at least one primer which is a nucleic acid of SEQ ID NO: 15, b) subjecting the nucleic acid and the primer to amplification conditions, and c) determining the presence or absence of amplification product.

71. A method for determining the presence or absence of SARS-associated corona virus in a sample, the method comprising:

a) contacting nucleic acid from a sample with at least one primer which is a nucleic acid of SEQ ID NO: 16, b) subjecting the nucleic acid and the primer to amplification conditions, and c) determining the presence or absence of amplification product.

* * * * *